United States Patent
Zeikus et al.

(10) Patent No.: US 7,105,329 B2
(45) Date of Patent: Sep. 12, 2006

(54) ACTINOBACILLUS SUCCINOGENES SHUTTLE VECTOR AND METHODS OF USE

(75) Inventors: J. Gregory Zeikus, Okemos, MI (US); Maris Laivenieks, East Lansing, MI (US); Claire Vieille, Lansing, MI (US); Pil Kim, Seoul (KR)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 11/042,925

(22) Filed: Jan. 25, 2005

(65) Prior Publication Data

US 2005/0164346 A1    Jul. 28, 2005

(51) Int. Cl.
*C12N 9/12* (2006.01)

(52) U.S. Cl. ...................................... 435/194
(58) Field of Classification Search ............... None
See application file for complete search history.

(56) References Cited

U.S. PATENT DOCUMENTS

| | | | |
|---|---|---|---|
| 5,143,833 | A | 9/1992 | Datta et al. |
| 5,573,931 | A | 11/1996 | Guettler et al. |
| RE37,393 | E | 9/2001 | Donnelly et al. |
| 6,420,151 | B1 | 7/2002 | Eikmanns et al. |
| 6,455,284 | B1 | 9/2002 | Gokarn et |
| 2003/0087381 | A1 | 5/2003 | Gokarn et |
| 2003/0113885 | A1 | 6/2003 | Lee et al. |

OTHER PUBLICATIONS

Leduc et al., Acta Crystallographica (2005) D61, 903-912.*
Matte et al., J. Mol. Biol. (1996) 256, 126-143.*
West, S.E., et al., Gene 160:81-86(1995).
Park, D.H., et al., J. Bacteriol. 181:2403-2410(1999).
Lalonde et al. (Am. J. Vet. Res. 50:1957-1960(1989).
Brogan, J.M., et al., Gene 169:141-142(1996).
Frey, J., Res. Microbiol. 143:263-269(1992).
Craig, F.F., et al., J. Gen. Microbiol. 135:2885-2890(1989).
Dixon, L.G., et al., Plasmid 32:228-232(1994).
Oswald, W., et al., FEMS Microbiol. Lett. 179:153-160(1999).
Wright, C. L., Plasmid 37:65-79 (1997).
Kehrenberg, C., et al., Antimicrob. Agents Chemother.42:2116-2118(1998).
West, S.E., et al., Gene 160:87-88 (1995).
Galli, D.M., et al., Plasmid 36:42-48 (1996).
Ishii, H., et al., Nippon Juigaku Zasshi 52:1-9 (1990).
Lalonde, G., et al., Gene 85:243-246(1989).
Nakano, Y., et al., Gene 169:139-140(1996).
Laivenieks, M., et al., Appl. Environ. Microbiol. 63:2273-2280(1997).
Shen, T.L., et al., J. Mass Spectrom. 34:1154-1165 (1999).
Brown, A.J.H., et al., Biotechniques 26:804-806(1999).
van der Werf, M.J., et al., Arch. Microbiol. 167:332-342(1997).

* cited by examiner

*Primary Examiner*—Nancy Vogel
(74) *Attorney, Agent, or Firm*—Ian C. McLeod

(57) ABSTRACT

An *Actinobacillus succinogenes* plasmid vector which provides a means to overexpress proteins in *A. succinogenes*. The plasmid can be transformed efficiently by electroporation, and replicates in a stable manner in *A. succinogenes*. The plasmid comprises at least one marker gene, operably linked to a first promoter functional in *Actinobacillus succinogenes*, an origin of replication functional in *Actinobacillus succinogenes*, a second promoter isolated from *Actinobacillus succinogenes*, and a cloning site downstream from the second promoter. Plasmids pLGZ901, pLGZ920, pLGZ921, and pLGZ922 are disclosed. The pckA gene polypeptide sequence and nucleic acid sequence of *Actinobacillus succinogenes*, including the promoter and ribosome binding site, is disclosed. Furthermore, a method for producing a recombinant *Actinobacillus succinogenes* is described, including a method of transformation. Additionally, a recombinant *Actinobacillus succinogenes* is disclosed and a method for producing succinate utilizing this recombinant *Actinobacillus succinogenes* is described.

1 Claim, 8 Drawing Sheets

```
                                                                                            90
TTAATTTCTTTAATCGGGACGCTATCGATAAATTGAAAATGCAGCAATAGAGGAAACACGGTTTGTTTGAGTGAAAACAGCCGTGTTTTT
                                                                                           180
TCATTTACCGCCATAAAAATTTGAAACGGATCACAAATCATGAAAAAAATACGTTCAAATTAGAACTAATTATCGAAAATTTGATCTAGT
                                                             -35              '-10     270
TAACATTTTTTAGGTATAAATAGTTTTAAAATAGATCTAGTTTGGATTTTTAATTTTAAATTATCAATGAGGTGAAGTATGACTGACTTA
              -35                    -10                RBS      M  T  D  L
                                                                                           360
AACAAACTCGTTAAAGAACTTAATGACTTAGGGCTTACCGATGTTAAGGAAATTGTGTATAACCCGAGTTATGAACAACTTTTCGAGGAA
 N  K  L  V  K  E  L  N  D  L  G  L  T  D  V  K  E  I  V  Y  N  P  S  Y  E  Q  L  F  E  E
                                                                                           450
GAAACCAAACCGGGTTTGGAGGGTTTCGATAAAGGGACGTTAACCACGCTTGGCGCGGTTGCCGTCGATACGGGGATTTTTACCGGTCGT
 E  T  K  P  G  L  E  G  F  D  K  G  T  L  T  T  L  G  A  V  A  V  D  T  G  I  F  T  G  R
                                                                                           540
TCACCGAAAGATAAATATATCGTTTGCGATGAAACTACGAAAGACACCGTTTGGTGGAACAGCGAAGCGGCGAAAAACGATAACAAACCG
 S  P  K  D  K  Y  I  V  C  D  E  T  T  K  D  T  V  W  W  N  S  E  A  A  K  N  D  N  K  P
                                                                                           630
ATGACGCAAGAAACTTGGAAAAGTTTGAGAGAATTAGTGGCGAAACAACTTTCCGGTAAACGTTTATTCGTGGTAGAAGGTTACTGCGGC
 M  T  Q  E  T  W  K  S  L  R  E  L  V  A  K  Q  L  S  G  K  R  L  F  V  V  E  G  Y  C  G
                                                                                           720
GCCAGTGAAAAACACCGTATCGGTGTGCGTATGGTTACTGAAGTGGCATGGCAGGCGCATTTTGTGAAAAACATGTTTATCCGACCGACC
 A  S  E  K  H  R  I  G  V  R  M  V  T  E  V  A  W  Q  A  H  P  V  K  N  M  F  I  R  P  T
                                                                                           810
GATGAAGAGTTGAAAAATTTCAAAGCGGATTTTACCGTGTTAAACGGTGCTAAATGTACTAATCCGAACTGGAAAGAACAAGGTTTGAAC
 D  E  E  L  K  N  F  K  A  D  F  T  V  L  N  G  A  K  C  T  N  P  N  W  K  E  Q  G  L  N
                                                                                           900
AGTGAAAACTTTGTCGCTTTCAATATTACCGAAGGTATTCAGCTTATCGGCGGTACTTGGTACGGCGGTGAAATGAAAAAAGGTATGTTC
 S  E  N  F  V  A  F  N  I  T  E  G  I  Q  L  I  G  G  T  W  Y  G  G  E  M  K  K  G  M  F
                                                                                           990
TCAATGATGAACTACTTCCTGCCGTTAAAAGGTGTGGCTTCCATGCACTGTTCCGCCAACGTAGGTAAAGACGGTGACGTGGCTATTTTC
 S  M  M  N  Y  F  L  P  L  K  G  V  A  S  M  H  C  S  A  N  V  G  K  D  G  D  V  A  I  F
                                                                                          1080
TTCGGTTTATCCGGTACGGGTAAACAACGCTTTCGACCGATCCTAAACGCCAATTAATCGGTGATGACGAACACGGTTGGGATGAATCC
 F  G  L  S  G  T  G  K  T  T  L  S  T  D  P  K  R  Q  L  I  G  D  D  E  H  G  W  D  E  S
                                                                                          1170
GGCGTATTTAACTTTGAAGGCGGTTGTTACGCGAAAACCATTAACTTATCTCAAGAAAACGAACCGGATATTTACGGCAATCCGTCGT
 G  V  F  N  F  E  G  G  C  Y  A  K  T  I  N  L  S  Q  E  N  E  P  D  I  Y  G  A  I  R  R
                                                                                          1260
GACGCATTATTAGAAAACGTCGTGGTTCGTGCAGACGGTTCCGTTGACTTTGACGACGGTTCAAAAACAGAAAATACCCGTGTTCATAT
 D  A  L  L  E  N  V  V  V  R  A  D  G  S  V  D  F  D  D  G  S  K  T  E  N  T  R  V  S  Y
                                                                                          1350
CCGATTTACCACATCGACAACATCGTTCGTCCGGTATCGAAAGCCGGTCATGCAACCAAAGTGATTTTCTTAACCGCGGACGCATTCGGC
 P  I  Y  H  I  D  N  I  V  R  P  V  S  K  A  G  H  A  T  K  V  I  F  L  T  A  D  A  F  G
                                                                                          1440
GTATTGCCGCCGGTTTCAAAACTGACTCCGGAACAAACCGAATACTACTTCTTATCCGCTTTACTGCAAAATTAGCGGGTACGGAACGC
 V  L  P  P  V  S  K  L  T  P  E  Q  T  E  Y  Y  F  L  S  G  F  T  A  K  L  A  G  T  E  R
                                                                                          1530
GGCGTAACCGAACCGACTCCGACATTCTCGGCCTGTTTCGGTGCGGCATTCTTAAGCCTGCATCCGATTCAATATGCGGACGTGTTGGTC
 G  V  T  E  P  T  P  T  F  S  A  C  F  G  A  A  F  L  S  L  H  P  I  Q  Y  A  D  V  L  V
                                                                                          1620
GAACGCATGAAAGCCTCCGGTGCGGAAGCTTATTTGGTGAACACCGGTTGGAACGGCACGGGTAAACGTATTTCAATCAAAGATACCCGC
 E  R  M  K  A  S  G  A  E  A  Y  L  V  N  T  G  W  N  G  T  G  K  R  I  S  I  K  D  T  R
                                                                                          1710
GGTATTATCGATGCGATTTTGGACGGTTCAATCGAAAAAGCGGAAATGGGCGAATTGCCAATCTTTAATTTAGCGATTCCTAAAGCATTA
 G  I  I  D  A  I  L  D  G  S  I  E  K  A  E  M  G  E  L  P  I  F  N  L  A  I  P  K  A  L
                                                                                          1800
CCGGGTGTTGATCCTGCTATTTTGGATCCGCGCGATACTTACGCAGACAAAGCGCAATGGCAAGTTAAAGCGGAAGATTTGGCAAACCGT
 P  G  V  D  P  A  I  L  D  P  R  D  T  Y  A  D  K  A  Q  W  Q  V  K  A  E  D  L  A  N  R
                                                                                          1890
TTCGTGAAAAACTTTGTGAAATATACGGCGAATCCGGAAGCGGCTAAATTAGTTGGCGCCGGTCCAAAAGCATAAAACTGTAAAAGCATA
 F  V  K  N  F  V  K  Y  T  A  N  P  E  A  A  K  L  V  G  A  G  P  K  A  ***
                                                                                          1980
GTATGTGCATGATTCGGTAAACTACCGAATAAAATCTGAAAAATAAGGCTGAGTATTTCCACTCAGCCTTTTGTTTTGGAAATTAGAAGT

TGTTTAGAAAGATAAACGGCGCGGCTTATTCGTCGTATTATTTGGGACATAAAAAACCCGTTGATAAA 2048
```

Figure 1

| Strain | Antibiotic resistance | Tetracycline concentration (μg/ml) | | | | | | | |
|---|---|---|---|---|---|---|---|---|---|
| | | 0 | 0.4 | 0.7 | 1.0 | 1.5 | 2.0 | 5.0 | 10.0 | 20.0 |
| 130Z (pLGZ921) | Tc$^R$ | + | + | + | + | + | + | 3-4 days | NG | NG |
| 130Z (pLGZ922) | Cm$^R$ | + | + | 2 days | 5-6 days | NG | NG | NG | NG | NG |

| Strain | Antibiotic resistance | Chloramphenicol concentration (μg/ml) | | | | | | | |
|---|---|---|---|---|---|---|---|---|---|
| | | 0 | 0.4 | 0.7 | 1.0 | 1.5 | 2.0 | 5.0 | 10.0 | 20.0 |
| 130Z (pLGZ921) | Tc$^R$ | + | + | NG | NG | NG | NG | NG | NG | NG |
| 130Z (pLGZ922) | Cm$^R$ | + | + | + | + | + | + | 2-3 days | NG | NG |

+: 0.5mm colonies developed overnight (<17 hours); NG: No growth.

Figure 9

ACTINOBACILLUS SUCCINOGENES SHUTTLE VECTOR AND METHODS OF USE

STATEMENT REGARDING FEDERALLY SPONSORED RESEARCH OR DEVELOPMENT

This research was supported by grants from the USDA (#00-34189-9045) and from the National Science Foundation NSF (#BES-0224596). The U.S. government has certain rights to this invention.

CROSS-REFERENCE TO RELATED APPLICATIONS

This application claims priority to Provisional application Ser. No. 60/492,804, filed Aug. 6, 2003.

BACKGROUND OF THE INVENTION (1) Field of the Invention

The present invention relates generally to plasmid vectors, and more particularly to *Actinobacillus succinogenes* plasmid vectors. The present invention further relates to overexpression of proteins in *A. succinogenes* and to engineered *A. succinogenes* strains which have the plasmids introduced into them.

(2) Description of the Related Art

Succinate has many industrial fine chemical uses. Succinate can also be used as an intermediary commodity chemical feedstock for producing bulk chemicals. Its greatest market potential might lie in its use as feedstock to produce stronger-than-steel plastics, biodegradable chelators, and green solvents. Most of the 17,000 tons (15,400 metric tons) of succinate sold per year are produced petrochemically from maleic acid. Succinate is also produced as a fine chemical by fermentation from glucose. For fermentation to be competitive in producing succinate as a commercial chemical, the overall production cost should be lowered from one (1) dollar per pound ($2.20 per kg) to approximately twenty (20) cents per pound (44 cents per kg).

U.S. Pat. No. 5,143,833 to Datta et al. teaches a method for producing succinic acid by growing a succinate producing *Anaerobiospirillum succiniciproducens* microorganism under specific conditions.

U.S. Reissued Patent No. RE37,393 to Donnelly et al. teaches a method for isolating succinic acid producing bacteria by increasing the biomass of an organism which lacks the ability to catabolize pyruvate and then growing the biomass in glucose-rich medium under an anaerobic environment to enable pyruvate-catabolizing mutants to grow. By using this method, Donnelly provides a mutant *E. coli* that produces high amounts of succinic acid. The mutant *E. coli* was derived from a parent which lacked the genes for pyruvate-formate lyase and lactate dehydrogenase.

U.S. Pat. No. 6,455,284 and U.S. Pat. Application Publication No. 2003/0087381, both to Gokarn et al. teach metabolic engineering to increase the carbon flow toward oxaloacetate to enhance production of bulk biochemicals, such as lysine and succinate, in bacterial and industrial fermentations. The carbon flow is redirected by genetically engineering bacteria to overexpress the enzyme pyruvate carboxylase.

U.S. Pat. Application Publication No. 2003/0113885 to Lee et al. teaches a novel microorganism, *Mannheimia* sp. 55E, capable of producing organic acids and a process using the microorganism for producing organic acids through anaerobic and aerobic incubations.

U.S. Pat. No. 6,420,151 to Eikmanns, et al. teaches an isolated nucleic acid from coryneform bacteria which encodes a phosphoenolpyruvate carboxykinase which is involved in production of succinate.

While the above methods can be used to produce succinate, *Actinobacillus succinogenes* is still the best succinate producer known. *Actinobacillus succinogenes* is a gram-negative capnophilic, anaerobic bacillus that belongs to *Pasteurellaceae*. *A. succinogenes* produces up to one hundred (100) grams per liter of succinate in optimized conditions. Much effort has been spent on engineering *Escherichia coli* strains to produce high succinate amounts, however none of the engineered *E. coli* strains surpassed *A. succinogenes* for succinate production. Carbon flow is stringently regulated in microorganism metabolism, including carbon flux towards oxaloacetate. Overcoming this control of carbon flux will possibly improve the yields of desirable products, such as succinate.

Previously, no genetic tools had been tested or developed that could be used for engineering *A. succinogenes* into an industrial succinate-producing strain. Therefore, it would be desirable to have a means to genetically engineer *A. succinogenes* to overproduce succinate. However, there is not yet a means for constructing recombinant *A. succinogenes*. The present invention provides a means for constructing recombinant *A. succinogenes* using a plasmid for the expression of proteins in *A. succinogenes*.

SUMMARY OF THE INVENTION

The present invention provides a plasmid comprising at least one marker gene operably linked to a first promoter functional in *Actinobacillus succinogenes*, an origin of replication functional in *Actinobacillus succinogenes*, a second promoter isolated from *Actinobacillus succinogenes*, and a cloning site downstream from the second promoter.

In further embodiments, the marker gene confers antibiotic resistance to *Actinobacillus succinogenes*. In further embodiments, the antibiotic is selected from the group consisting of ampicillin, chloramphenicol, tetracycline, and erythromycin.

In further embodiments, the second promoter is from the pckA gene of *Actinobacillus succinogenes*. In some embodiments, the second promoter comprises substantially the nucleic acid sequence set forth in SEQ ID NO: 21 from between about nucleotide 25 and nucleotide 255. In further still embodiments, the second promoter provides a ribosome binding site comprising the nucleotide sequence AGGTG. In further still embodiments, the plasmid further comprises a ColE1 origin of replication. In further still embodiments, the cloning site comprises one or more restriction endonuclease cleavage sites.

The present invention also provides a plasmid which is pLGZ901 and a plasmid which is pLGZ920 (ATCC PTA-6140 deposited on Aug. 3, 2004)

The present invention further provides a polypeptide which comprises an amino acid sequence substantially similar to the amino acid sequence set forth in SEQ ID NO. 22. The present invention still further provides a nucleic acid which comprises a nucleotide sequence substantially similar to the nucleotide sequence set forth in SEQ ID NO: 21.

The present invention further provides a method for producing a recombinant *Actinobacillus succinogenes* comprising providing a plasmid comprised of at least one marker gene operably linked to a first promoter functional in *Actinobacillus succinogenes*, an origin of replication for the plasmid functional in *Actinobacillus succinogenes*, a second promoter isolated from *Actinobacillus succinogenes*, and a cloning site for a nucleic acid downstream of the second promoter, transforming an *Actinobacillus succinogenes* with the plasmid, and selecting the recombinant *Actinobacillus succinogenes* from non-transformed *Actinobacillus succinogenes*.

In some embodiments of the method, the transformation is electroporation. In some embodiments of the method, the marker gene confers antibiotic resistance to the recombinant *Actinobacillus succinogenes*. In further embodiments of the method, the antibiotic is ampicillin, tetracycline, or chloramphenicol. In some embodiments of the method, the recombinant *Actinobacillus succinogenes* is selected from non-transformed *Actinobacillus succinogenes* by culturing in the presence of the antibiotic. In some embodiments of the method, the second promoter is from the pckA gene of *Actinobacillus succinogenes*. In some embodiments of the method, the second promoter comprises substantially the nucleic acid sequence set forth in SEQ ID NO: 21 from between about nucleotide 25 and nucleotide 255. In some embodiments of the method, the second promoter provides a ribosome binding site comprising the nucleotide sequence AGGTG. In some embodiments of the method, the plasmid further includes a ColE1 origin of replication. In some embodiments of the method, the plasmid is pLGZ901 or pLGZ920.

The present invention further provides a recombinant *Actinobacillus succinogenes* comprising a plasmid capable of autonomous replication in *Actinobacillus succinogenes* which comprises at least one selectable marker gene and the *Actinobacillus succinogenes* pckA gene. In some embodiments of the recombinant *Actinobacillus succinogenes*, the pckA gene comprises the nucleic acid sequence set forth in SEQ ID NO: 21. In some embodiments of the recombinant *Actinobacillus succinogenes*, the plasmid is pLGZ902. In some embodiments of the recombinant *Actinobacillus succinogenes*, the marker gene confers ampicillin, tetracycline, or chloramphenicol resistance to the recombinant *Actinobacillus succinogenes*.

The present invention further provides a method for producing succinate comprising providing a recombinant *Actinobacillus succinogenes* comprising a plasmid capable of autonomous replication in *Actinobacillus succinogenes* which comprises at least one selectable marker gene and a recombinant gene expressed under the control of the *Actinobacillus succinogenes* pckA promoter, providing a growth medium for culturing the recombinant *Actinobacillus succinogenes*, and culturing the recombinant *Actinobacillus succinogenes* in the growth medium to produce the succinate.

In some embodiments of the method the promoter comprises substantially the nucleic acid sequence set forth in SEQ ID NO: 21 from between about nucleotide 25 and nucleotide 255. In some embodiments of the method the plasmid is pLGZ901, and in further embodiments the plasmid is pLGZ920. In some embodiments of the method the marker gene confers ampicillin, tetracycline, or chloramphenicol resistance to the recombinant *Actinobacillus succinogenes*. In some embodiments of the method the growth medium comprises ampicillin, tetracycline, or chloramphenicol.

In further embodiments of the method the recombinant *Actinobacillus succinogenes* is a mutant strain in which an *Actinobacillus succinogenes* gene which inhibits succinate production comprises a deletion. In further embodiments of the method the *Actinobacillus succinogenes* gene further comprises a selectable marker under the control of the *Actinobacillus succinogenes* pckA promoter. In further embodiments of the method the selectable marker gene confers resistance to an antibiotic selected from the group consisting of chloramphenicol and tetracycline to the mutant *Actinobacillus succinogenes* strain.

The present invention further provides a recombinant microorganism comprising the nucleic acid which comprises a nucleotide sequence substantially similar to the nucleotide sequence set forth in SEQ ID NO: 21.

The present invention further provides a plasmid which is pLGZ921, and a plasmid which is pLGZ922.

Objects

Therefore, it is an object of the present invention to provide a method for producing recombinant *Actinobacillus succinogenes*.

It is a further object of the present invention to provide a plasmid which replicates in *A. succinogenes*.

It is further still an object of the present invention to provide a recombinant *A. succinogenes* which overexpresses proteins.

These and other objects will become increasingly apparent by reference to the following description and the drawings.

BRIEF DESCRIPTION OF THE DRAWINGS

FIG. 1 illustrates the nucleotide sequence SEQ ID NO: 21 of *A. succinogenes* pckA and deduced amino acid sequence SEQ ID NO: 22 of PEPCK. Two pairs of putative −35 and −10 promoter regions are underlined. The putative ribosome binding site (RBS) is in bold. The stop codon is indicated by three asterisks. The GenBank accession number for the nucleotide sequence is AY308832.

FIG. 9 illustrates the time for plasmid-harboring *A. succinogenes* to form colonies on TS agar at 37° Celsius in the presence of tetracycline or chloramphenicol.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control. The plasmids pLGZ901, pLGZ920, pLGZ921, and pLGZ922 are available upon request from Michigan State University.

Definitions for the following terms are provided to promote a further understanding of the present invention.

The term "marker" refers to sequences which encode a gene product, usually an enzyme, that inactivates or otherwise detects or is detected by a compound in the growth medium. For example, the inclusion of a marker sequence can render the transformed cell resistant to an antibiotic, or it can confer compound-specific metabolism on the transformed cell. Marker genes can confer resistance to antibiotics including, but not limited to, ampicillin, chloramphenicol, tetracycline, and erythromycin.

Figure 6:
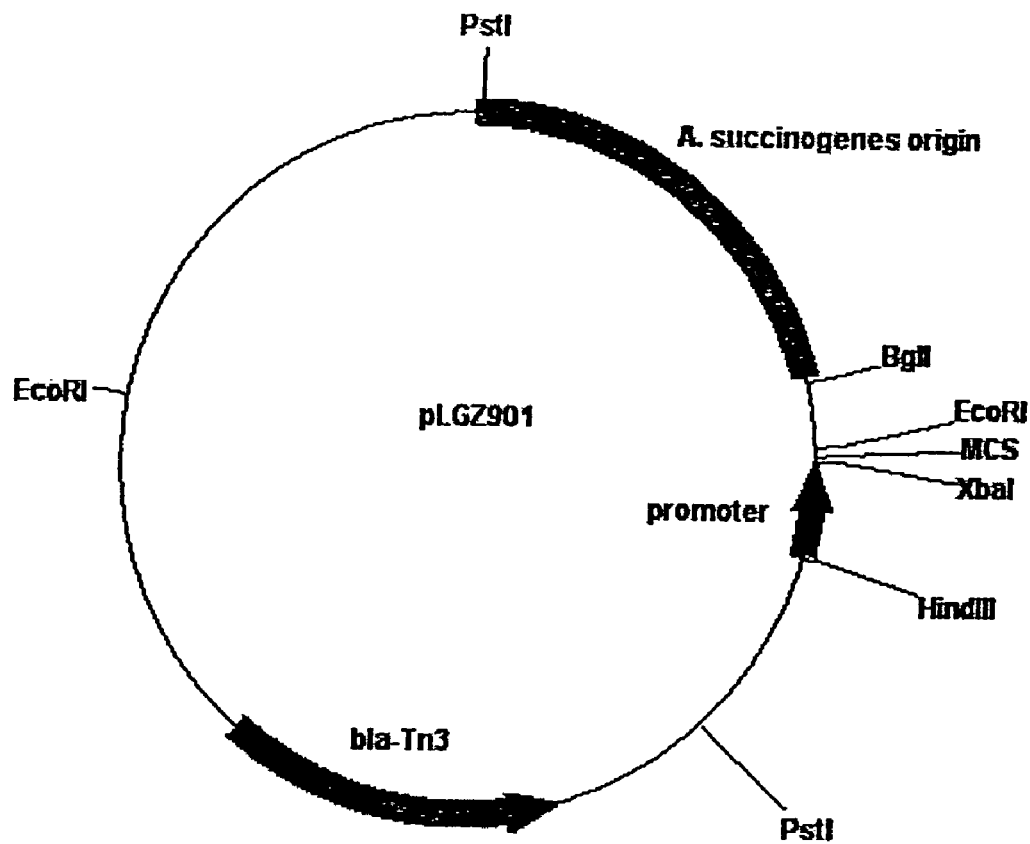
FIG. 6 illustrates the physical map of the pLGZ901 plasmid. The origin of replication functional in *A. succinogenes*, the cloning site (MCS), the *A. succinogenes* promoter, and the bla-Tn3 marker gene are shown.

The term "pLGZ901" refers to the plasmid construct as represented by FIG. 6 . The plasmid is available upon request from Michigan State University.

Figure 7:
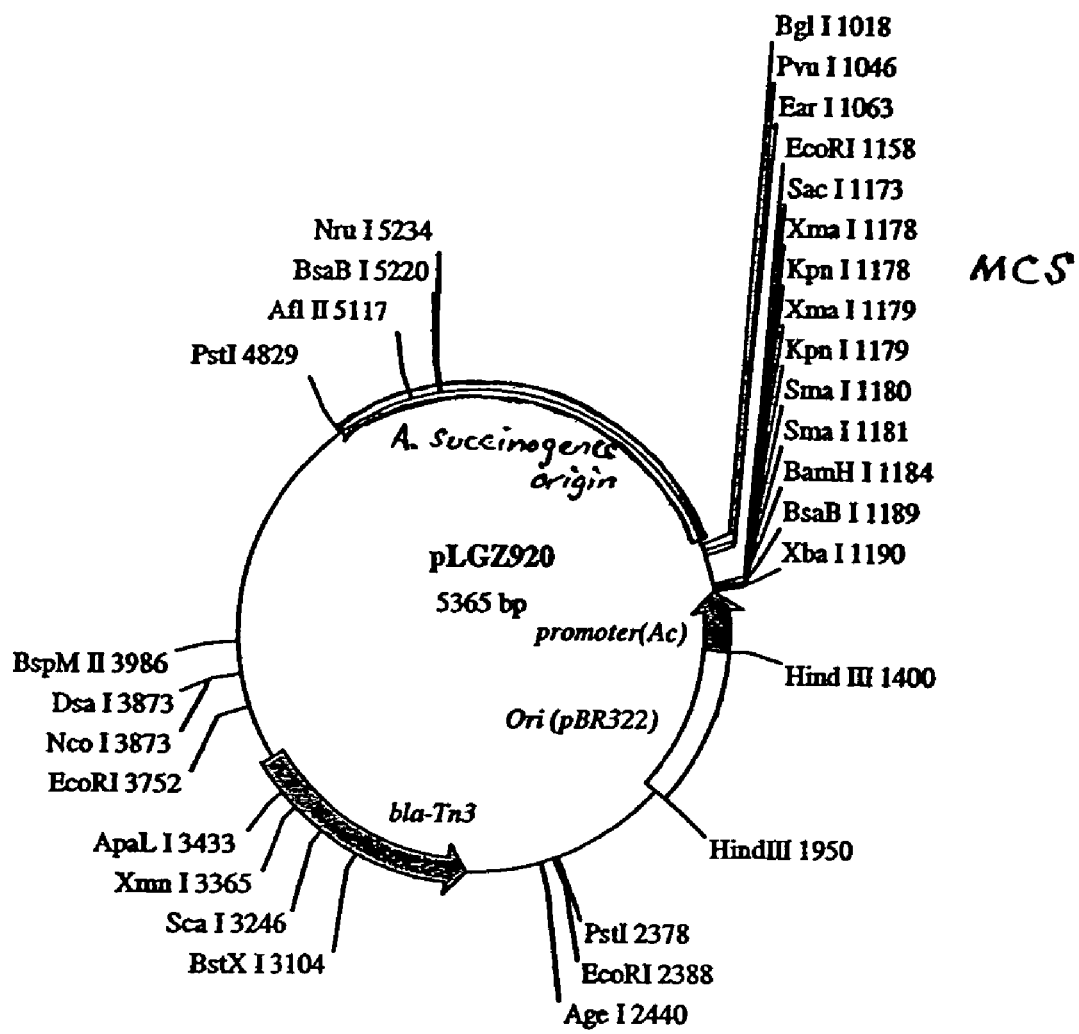
FIG. 7 illustrates the physical map of the *E. coli-A. succinogenes* shuttle vector pLGZ920. The ColE1 origin of replication, the origin of replication functional in *A. succinogenes*, the cloning site (MCS), the *A. succinogenes* promoter, and the bla-Tn3 marker gene are shown.
Figure 8:
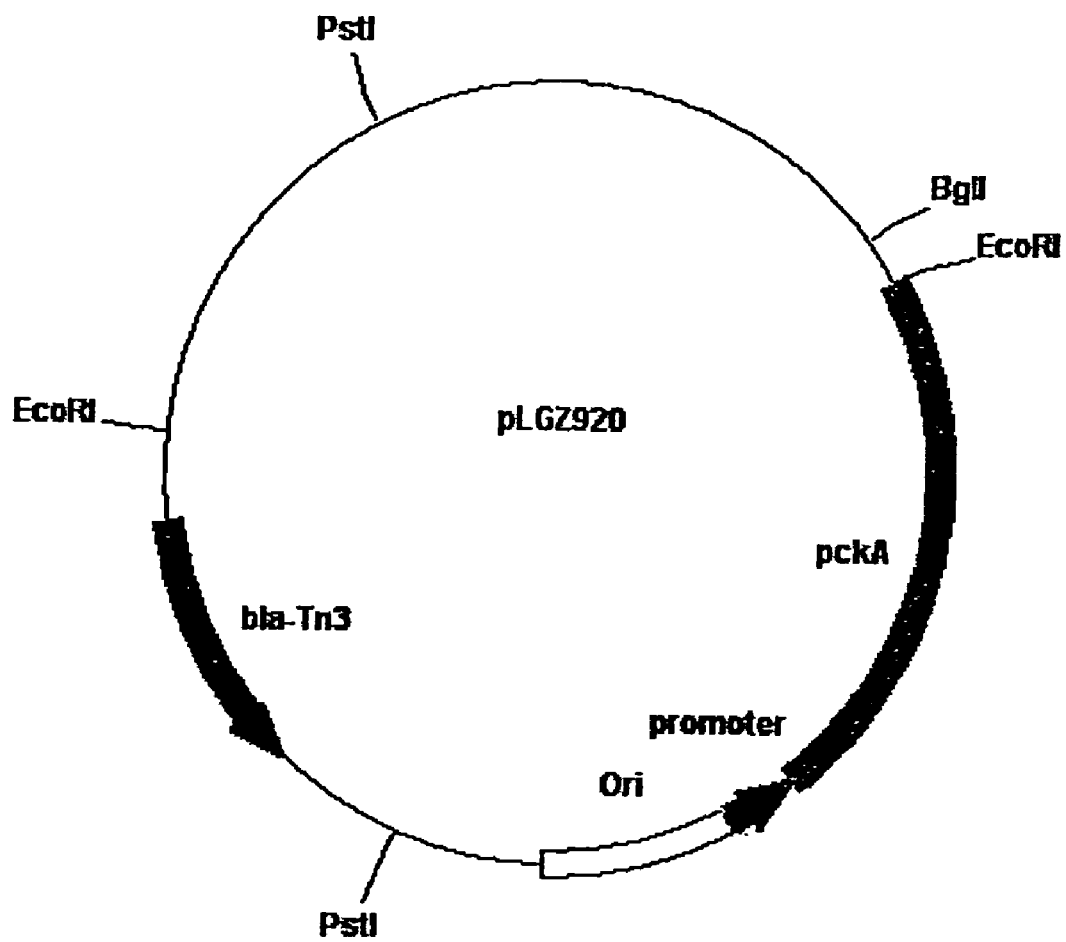
FIG. 8 illustrates the physical map of the pLGZ920 plasmid with an inserted pckA gene. The ColE1 origin of replication, the origin of replication functional in *A. succinogenes*, the cloning site (MCS), the *A. succinogenes* promoter, the pckA gene, and the bla-Tn3 marker gene are shown.

The term "pLGZ920" refers to the plasmid construct as represented by FIG. 7. The plasmid is available upon request from Michigan State University, and has been deposited under the terms of the Budapest Treaty at the ATCC, Manassas, Va. on Aug. 3, 2004, with accession number PTA-6140.

The term "promoter" refers to a DNA fragment to which ribonucleic acid polymerase binds to initiate the transcription of nucleic acid sequences linked to the promoter.

A promoter is "operably linked" to a nucleic acid sequence if it can be used to control or regulate transcription of the nucleic acid sequence.

The term "origin of replication" refers to a nucleic acid sequence which is necessary to allow replication of a plasmid within an organism.

The term "cloning site" refers to a region which allows for the insertion of desired nucleic acid sequences. Typically, the cloning site comprises one or more restriction endonuclease recognition sites. Cloning sites include, but are not limited to, multiple cloning sites or polylinkers.

The term "ribosome binding site" refers to a short nucleotide sequence to which the ribosome binds upon the transcribed ribonucleic acid.

The term "transformation" means the process of introducing DNA into an organism which changes the genotype of the recipient organism.

The term "PEPCK" refers to phosphoenolpyruvate carboxykinase.

The term "vector" refers to a deoxyribonucleic acid which is capable of replication and also capable of incorporating desired deoxyribonucleic acid fragments for cloning. Vectors include plasmids, cosmids, phages, and yeast artificial chromosomes.

The term "shuttle vector" refers to a vector able to replicate in two different organisms.

A required step toward *A. succinogenes* metabolic engineering is developing genetic tools. It is necessary to be able to increase the expression level of certain enzymes, probably by introducing them on stable, multicopy plasmids, and to shut down some pathways by generalized or targeted mutagenesis. One method for producing succinate can comprise a mutant strain of *A. succinogenes* in which a selected gene which minimizes succinate production contains a deletion. Another method for producing succinate can comprise both increasing expression levels of some enzymes by introducing them on plasmids, and shutting down a pathway which minimizes succinate production in which a selected gene contains a deletion. The tools needed to achieve this include (i) selection markers, (ii) a transformation and/or conjugation system(s), (iii) a complementation system, and (iv) targeted and generalized mutagenesis systems.

Figure 5:
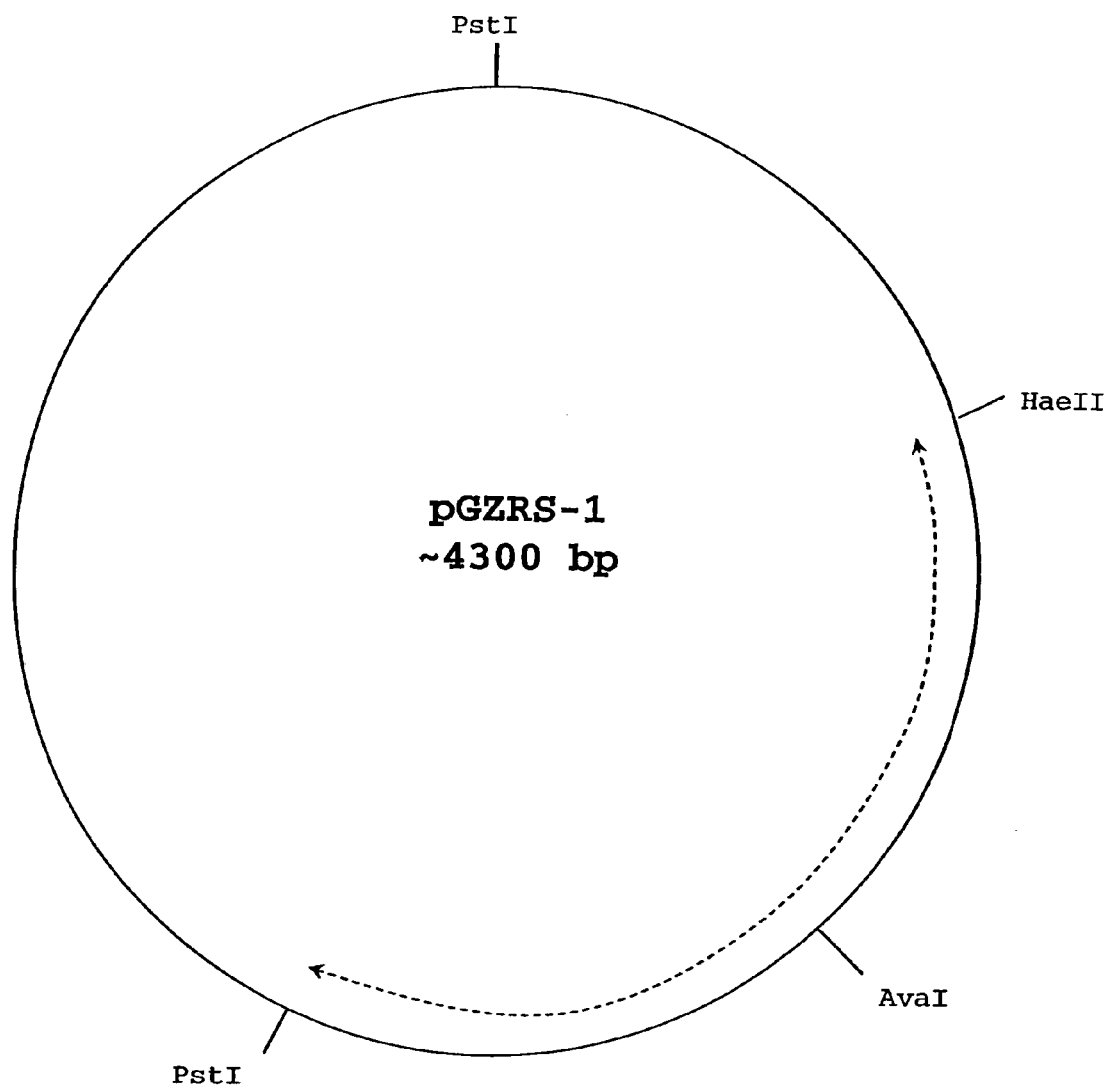
FIG. 5 illustrates the physical map of the pGZRS-1 plasmid. The dashed line represents the minimum region required for replication in *A. pleuropneumoniae*.

A plasmid was developed suitable for use in *A. succinogenes* to express proteins. First, a replicon that stably replicates in *A. succinogenes* was found. *A. succinogenes* can be transformed by electroporation at reasonably high efficiency by pGZRS-19, pGZRS-19 replicates in a stable manner in *A. succinogenes*, and the ampicillin resistance gene carried by pGZRS-19 is expressed in *A. succinogenes*. These properties made pGZRS-19 an excellent starting point to develop an *E. coli-A. succinogenes* shuttle vector to be used for expressing foreign proteins in *A. succinogenes*. The plasmid pGZRS-19 was constructed from pGZRS-1, illustrated in FIG. 5, which is a member of the H2 class of Apl plasmids. The pGZRS-1 plasmid is an endogenous *Actinobacillus pleuropneumoniae* (Apl) 4.3 kilobase plasmid found in the serotype 7 strain EL312. (West, S. E., et al., Gene 160:81–86(1995)). The plasmid pGZRS-19 carries the multiple cloning site from pUC19, and the bla gene from Tn3 under the control of a putative Apl promoter. The plasmid pGZRS-19 replicates in Apl, *Escherichia coli*, *Pasteurella haemolytica*, and *Haemophilus (Actinobacillus) actinomycetemcomitans*. West et al. demonstrated that there is a minimal region required for replication in both Apl and *E. coli*, which is within the 1.5 kB PstI-HaeII fragment of pGZRS-1. We demonstrated that *A. succinogenes* is transformed by electroporation at reasonably high efficiency, that pGZRS-19, with this fragment, replicates in a stable manner in *A. succinogenes*, and that the ampicillin resistance gene carried by pGZRS-19 is expressed in *A. succinogenes*.

Three steps were required to develop this new vector. (i) A gene that we knew was constitutively expressed at high levels in *A. succinogenes* (i.e., the pckA gene) was cloned and sequenced. (ii) Its promoter region and ribosome binding site were subcloned into pGZRS-19. A unique XbaI site was included immediately downstream of the pckA ribosome binding site to facilitate the cloning of foreign genes under control of the pckA promoter. (iii) Finally, the ColE1 origin of replication was added to the vector to increase its stability in *E. coli*. High levels of β-galactosidase and PEPCK activities detected in cultures of recombinant *A. succinogenes* strains confirmed that both *A. succinogenes* and foreign proteins could be expressed in *A. succinogenes* under control of the *A. succinogenes* pckA promoter carried by our pGZRS-19-derived vector, pLGZ920.

EXAMPLE 1

Bacterial strains and plasmids used in this study are listed in Table 1.

2403–2410 (1999)). *A. succinogenes* strains were grown in Trypticase-Soy (TS) broth (Becton-Dickinson, Cockeyville, Md.) or medium A (per liter: 9 g glucose, 10 g sodium bicarbonate, 5 g yeast extract, 8.5 g $NaH_2PO_4.H_2O$, and 15.5 g $K_2HPO_4$). The pH was adjusted to 7.5 with NaOH before autoclaving, leading to a pH of 7.0 after autoclaving. The glucose was added aseptically after sterilization. *A. succinogenes* cultures were grown in butyl-rubber-stopper 18-ml anaerobic tubes and 158-ml serum vials containing 10 ml and 100 ml medium, respectively. When grown on plates, *A. succinogenes* strains were grown in an anaerobic jar under $CO_2$ atmosphere.

EXAMPLE 2

Antibiotic minimum inhibitory concentrations. To determine the sensitivity of *A. succinogenes* 130Z to antibiotics, the growth of *A. succinogenes* 130Z was tested in medium A (liquid medium) containing a series of antibiotics commonly used in bacteriology. Antibiotics and antibiotic concentrations used are listed in Table 2. One ml of 130Z preculture was inoculated into 9 ml of medium A containing

TABLE 1

| Plasmid | Relevant characteristics | References |
| --- | --- | --- |
| pCR ™ II | TOPO TA cloning vector | Invitrogen, Carlsbad, CA |
| pCR2.1 | TOPO TA cloning vector | Invitrogen |
| pUC19 | $Amp^R$, lacZα, ColE1 multicopy cloning vector | Invitrogen |
| pProEx-1 | $Amp^R$, ColE1 multicopy cloning vector | [Bolivar, 1978 #3323] |
| pBR325 | $Amp^R$, $Cm^R$, $Tet^R$, ColE1 cloning vector | Laboratory collection |
| pGZRS-19 | pGZRS-1 replicon, $Amp^R$ (Tn3), replicates in Aple, Phae, Aact, Replicates in *E. coli*, pUC18/19 multiple cloning site, lacZα-complementation | (30) |
| pGZRS-30 | pGZRS-1 replicon, $Km^R$ (Tn903), $Cm^R$ (Tn9) | (30) |
| UB214 | Mannheimia haemolytica pMHT1 replicon, $Tet^R$ | (17) |
| pLGZ901 | pGZRS-19 derivative, *A. succinogenes* pckA promoter | This study |
| pLGZ902 | pGZRS-19 derivative, *A. succinogenes* pckA gene | This study |
| pLGZ903 | pGZRS-19 derivative, *E. coli* lacZα under control of the *A. succinogenes* pckA promoter | This study |
| pLGZ920 | pGZRS-19 derivative, *A. succinogenes* pckA promoter, pGZRS-1 and ColE1 replicons | This study |
| pLGZ921 | pLGZ920 derivative, pBR325 $Cm^R$ under control of the *A. succinogenes* pckA promoter | This study |
| pLGZ922 | pLGZ920 derivative, pBR325 $Tet^R$ under control of the *A. succinogenes* pckA promoter | This study |
| pGZRS-19/UB214 | Fusion of pLGZ901 and UB214 plasmids | This study |
| UB214-$Amp^R$ | UB214 derivative containing $Amp^R$ from pGZRS-19 | This study |

*E. coli* DH5α and JM110 were used for plasmid construction. *E. coli* strains were grown in LB medium (Sambrook, J., et al., Molecular Cloning: a Laboratory Manual, $2^{nd}$ ed. Cold Spring Harbor Laboratory Press, Cold Spring Harbor, N.Y. (1989)) supplemented with antibiotics (at 50 μg/ml) when necessary. *A. succinogenes* 130Z (ATCC 55618) and its derivative FZ6 were obtained as gifts from MB1 International (Lansing, Mich.). Strain FZ6 is a succinate-overproducing mutant that was selected by resistance to fluoroacetate (Guettler, M. V., et al., U.S. Pat. No. 5,573,931 (1996)). FZ6 produces only pyruvate and succinate as fermentation products from glucose. FZ6 lacks pyruvate-formate lyase activity (Park, D. H., et al., J. Bacteriol. 181:

each antibiotic and incubated at 37° C. for 7 days. Cell growth was followed by measuring $OD_{660}$.

TABLE 2

Antibiotics and antibiotic concentrations used in this study.

| Antibiotic | Concentrations tested in liquid cultures (μg/ml) | Concentration used in plates after transformation (μg/ml) |
| --- | --- | --- |
| Ampicillin | 5, 10, 25, 50 | 25 |
| Chloramphenicol | 1, 2.5, 5, 10 | 2.5 |
| Tetracyclin | 5, 10, 20, 30 | 10 |

TABLE 2-continued

Antibiotics and antibiotic concentrations used in this study.

| Antibiotic | Concentrations tested in liquid cultures (µg/ml) | Concentration used in plates after transformation (µg/ml) |
|---|---|---|
| Erythromycin | 5, 10, 20 | 10 |
| Streptomycin | 30 | Not used |
| Kanamycin | 50 | Not used |

Resistance of A. succinogenes to antibiotics. Growth of A. succinogenes 130Z was tested in the presence of antibiotics at the concentrations listed in Table 2. A. succinogenes 130Z grew perfectly well in the presence of 50 µg/ml kanamycin or 30 µg/ml streptomycin. Very slow growth was observed in the presence of 5 µg/ml ampicillin or 5 µg/ml erythromycin ($OD_{660}$ of approximately 0.05 after 7 days culture). No growth was detected in the presence of 10 µg/ml ampicillin, 1 µg/ml chloramphenicol, 5 µg/ml tetracycline, or 10 µg/ml erythromycin. A. succinogenes is sensitive to low concentrations of ampicillin, chloramphenicol, erythromycin, and tetracycline, so the corresponding resistance genes (i.e., $Amp^R$, $Cm^R$, $Tet^R$, and $Ery^R$) could be used as selection markers on plasmids used to transform A. succinogenes. We discovered that the Tn3 $Amp^R$ gene carried by pGZRS-19 is naturally expressed in A. succinogenes.

EXAMPLE 3

A. succinogenes 130Z (ATCC 55618) was used as the host strain. One hundred ml of actively growing cells in TS broth ($OD_{660}$ of 0.3) were chilled on ice and harvested by centrifugation at 4,000×g for 10 minutes at 4° C. Cells were washed twice with 5 ml of ice-cold 15% glycerol and resuspended in 0.2 ml of ice-cold 15% glycerol. Fifty microliters (µl) of this cell suspension was mixed with 0.5–1 microgram (µg) plasmid in a chilled, 2.0 mm Gene pulser cuvette (BioRad, Richmond, Calif.). Electroporation was performed at 2.5 kV, 200 Ω, and 25 µF. One milliliter (ml) of TS broth was immediately added to the electroporated cells. The suspension was incubated for 1 hour (hr) at 37° C. and then spread (under air) on TS agar plates containing ampicillin, chloramphenicol, or tetracycline (concentrations listed in Table 2). Plates were incubated in an anaerobic jar under $CO_2$ atmosphere at 37° C. for 24–48 hr. A. pleuropneumoniae-E. coli shuttle vectors, pGZRS-19 and pGZRS-30 were provided by Dr. Susan West (Department of Pathobiological Sciences, School of Veterinary Medicine, University of Wisconsin-Madison, Madison, Wis. 53706). Shuttle vector UB214 was provided by Dr. Stefan Schwarz (fur Tierzucht and Tierverhalten der Bundesforschungsantalt für Landwirtschaft Braunschweig (FAL), Dörnbergstr 25–27, 29223 Celle, Germany).

Introduction of plasmids into bacteria can be done using any means known in the art, including, but not limited to, electroporation, chemical transformation, conjugation, liposome mediated gene transfer, and particle bombardment. Actinobacillaceae are naturally non-transformable. Lalonde et al. (Am. J. Vet. Res. 50:1957–1960 (1989)) were the first to develop electroporation in A. pleuropneumoniae. Electroporation has since been used extensively to transform various Actinobacillus, Haemophilus, and Pasteurella strains with efficiencies of up to $3.10^6$–$10^7$ (Brogan, J. M., et al., Gene 169:141–142(1996); Frey, J., Res. Microbiol. 143:263–269 (1992)). Conditions typically used include a capacitance set at 25 µF, a pulse controller at 200–1000 Ω, and a pulse amplitude of 2.5 to 6.5 kV/cm (Craig, F. F., et al., J. Gen. Microbiol. 135:2885–2890 (1989); Dixon, L. G., et al., Plasmid 32:228–232 (1994); Frey, J., Res. Microbiol. 143:263–269 (1992); Lalonde, G., et al., Am. J. Vet. Res. 50:1957–1960 (1989); Oswald, W., et al., FEMS Microbiol. Lett. 179:153–160 (1999); West, S. E., et al., Gene 160: 81–86 (1995); Wright, C. L., Plasmid 37:65–79 (1997)). The electroporation conditions (i.e., 2.5 kV, 200 Ω, and 25 µF) that are standard for E. coli, and that are among the typical conditions used for Actinobacillaceae.

Because the organization of Actinobacillaceae promoters is different from that of E. coli promoters (Doree, S. M., et al. J. Bacteriol. 183:1983–1989 (2001)), most antibiotic resistance genes that have been successfully used in Pasteurellaceae shuttle vectors originate from transposons or from Actinobacillus indigenous plasmids. We first tested ampicillin, chloramphenicol, and tetracyclin resistance ($Amp^R$, $Cm^R$, and $Tet^R$, respectively) genes that are known to be expressed in Pasteurellaceae species (Craig, F. F., et al., J. Gen. Microbiol. 135:2885–2890 (1989); Kehrenberg, C., et al., Antimicrob. Agents Chemother. 42:2116–2118 (1998); West, S. E., et al., Gene 160:87–88 (1995); West, W. E., et al., Gene 160:81–86 (1995); Wright, C. L., et al., Plasmid 37:65–79(1997)).

A number of plasmids have been isolated from Pasteurellaceae or have been constructed as vectors for Pasteurellaceae species (Craig, F. F., et al., J. Gen. Microbiol. 135:2885–2890 (1989); Dixon, L. G., et al., Plasmid 32:228–232 (1994); Frey, J., Res. Microbiol. 143:263–269 (1992); Galli, D. M., et al., Plasmid 36:42–48 (1996); Ishii, H., et al., Nippon Juigaku Zasshi 52:1–9 (1990); Kehrenberg, C., et al., Antimicrob. Agents Chemother. 42:2116–2118 (1998); Lalonde, G., et al., Gene 85:243–246 (1989); Nakano, Y., et al., Gene 169:139–140 (1996); West, S. E., et al., Gene 160:87–88 (1995); West, S. E., et al., ene 160:81–86 (1995); Wright, C. L., et al., Plasmid 37:65–79 (1997)). We tested three replicons for their ability to replicate in A. succinogenes.

Efficiency of electroporation of A. succinogenes with plasmids pGZRS-19, pGZRS-30, and UB214 was used to determine the ability of these plasmids to replicate and to express their antibiotic resistance genes in A. succinogenes. Electroporation of A. succinogenes with pGZRS-19 gave an average of $5.4 \times 10^4$ CFU/µg plasmid (Table 4). No significant difference was observed in the transformation yields obtained using pGZRS-19 DNA purified from E. coli and A. succinogenes strains (Table 4), suggesting that A. succinogenes does not have a restriction system inhibiting transformation.

TABLE 4

Efficiency of electroporation of A. succinogenes and
E. coli with pGZRS-19 and its derivatives

| | CFU/μg plasmid | | | | | |
|---|---|---|---|---|---|---|
| | PGZRS-19 | | pLGZ901 | | pLGZ903 | |
| Host | [a]Eco | [b]Acs | Eco | Acs | Eco | Acs |
| A. succinogenes | | | | | | |
| 130Z | $6.2 \times 10^4$ | $5.6 \times 10^4$ | $5.1 \times 10^4$ | $7.2 \times 10^4$ | $2.4 \times 10^4$ | $4.2 \times 10^4$ |
| FZ6 | $5.9 \times 10^4$ | $3.9 \times 10^4$ | $3.5 \times 10^4$ | $3.6 \times 10^4$ | $2.0 \times 10^4$ | $2.5 \times 10^4$ |
| E. coli | | | | | | |
| DH5α | $5.6 \times 10^6$ | $6.3 \times 10^6$ | $7.2 \times 10^6$ | $7.3 \times 10^6$ | $4.7 \times 10^6$ | $5.4 \times 10^6$ |
| JM110 | $1.8 \times 10^6$ | $4.2 \times 10^6$ | $2.6 \times 10^6$ | $1.8 \times 10^6$ | $1.7 \times 10^6$ | $1.8 \times 10^6$ |

[a]Eco: The plasmid DNA used for transformation was purified from E. coli;
[b]Acs: The plasmid DNA used for transformation was purified from A. succinogenes.

A. succinogenes transformants containing pGZRS-19 did not show any colonies after 48 hours on plates containing 100 μg/ml ampicillin, so ampicillin at 25 μg/ml was used in the selection medium. No colonies were obtained after transformation of A. succinogenes with pGZRS-30, using the antibiotic concentrations listed in Table 2. While the A. pleuropneumoniae-E. coli shuttle vector pGZRS-19 was stably mainained and its $Tn_3$ $Amp^r$ gene was expressed in A. succinogenes, attempts at identifying other replicons that are maintained and other antibiotic resistance genes that are expressed in A. succinogenes were not. The M. haemolytica pMHT1 replicon (tested using the UB214 $Amp^R$ construct) was unable to replicate in A. succinogenes. In contrast to the Tn3 $Amp^R$ gene, the Tn9 $Cm^R$ gene carried by pGZRS-30 and the $Tet^R$ gene carried by UB214 (tested in the pGZRS-19/UB214 construct) were not expressed from their own promoters in A. succinogenes. Once expressed under a functional promoter (i.e. the pckA promoter), though, we determined that $Cm^R$ and $Tet^R$ were functional and that they could be used as selection markers in A. succinogenes. These selection markers can be used to label knock-out mutations.

Because transformation of A. succinogenes with pGZRS-19 was successful, our lack of success with pGZRS-30 most probably comes from the inability of the $Cm^R$ gene of Tn9 to be expressed in A. succinogenes. In the case of plasmid UB214, the absence of transformants could be due either to the inability of the plasmid to replicate in A. succinogenes, or to the inability of its antibiotic resistance gene to be expressed in A. succinogenes. To determine whether UB214 (i.e., the M. haemolytica pMHT1 replicon) can replicate in A succinogenes, we constructed the UB214-$Amp^R$ derivative. In this plasmid, the 1.4 kb EcoRI fragment carrying the $Amp^R$ gene of pGZRS-19 was subcloned into the unique EcoRI site of UB214. UB214-$Amp^R$ conferred ampicillin resistance to E. coli, but A. succinogenes transformed with UB214-$Amp^R$ did not show any colonies after 48 hours on ampicillin (25 μg/ml) plates. To determine whether the $Tet^R$ gene carried by UB214 is expressed in A. succinogenes, the whole UB214 plasmid was cloned into the unique BamHI site of pGZRS-19. The pGZRS-19/UB214 construct conferred both ampicillin and tetracycline resistance to E. coli. A. succinogenes transformed with pGZRS-19/UB214 showed many colonies after 48 hours on ampicillin (25 μg/ml) plates, but none on tetracycline (5 μg/ml) plates. These results indicate that not only is the M. haemolytica pMHT1 replicon unable to replicate in A. succinogenes, but its $Tet^R$ gene is also not expressed from its own promoter in A. succinogenes.

EXAMPLE 4

Plasmid DNA purification, PCR amplification, restriction analysis, subcloning, transformation, and bacterial culture utilized methods generally described in Sambrook, J., Fritsh, E. F., and Maniatis, T., *Molecular Cloning: A Laboratory Manual*. 2nd ed., Cold Spring Harbor Laboratory Press, N.Y. (1989); and Ausubel, F. M., et al., Current Protocols in *Molecular Biology* Volumes 1–3, John Wiley & Sons, Inc., N.Y. (1993–1998). Oligonucleotides used for PCR reactions and for sequencing were synthesized by the Michigan State University Macromolecular Structure, Sequencing, and Synthesis Facility. DNA sequencing was performed by the Michigan State University Genomics Technology Support Facility. DNA was recovered from agarose gels with the Geneclean II kit (BIO 101, La Jolla, Calif.).

The A. succinogenes pckA gene was cloned in 4 steps. In step (i), an alignment of E. coli, Anaerobiospirillum succiniciproducens, Haemophilus influenzae, Rhizobium sp. NGR234, and *Vibrio cholerae* PEPCks sequences (Genbank accession Nos. F65135, U95960, NP_438969, S18606, and Q9KNK0, respectively) indicated that sequences YGGEMKK, SEQ ID NO: 23, and NTGWNG, SEQ ID NO: 24, were highly conserved. Degenerate oligonucleotides SEQ ID NO: 1 and SEQ ID NO: 2 (Table 3) were used as primers to amplify a pckA internal fragment using A. succinogenes 130Z chromosomal DNA as the template. The 0.7 kb PCR product was cloned into pCR™II (Invitrogen, Carlsbad, Calif.) and sequenced. For step (ii), A. succinogenes PEPCK was purified to homogeneity as described (Shen, T. L., et al., J. Mass Spectrom. 34:1154–1165 (1999)) and submitted to N-terminal sequencing (performed by the Michigan State University Macromolecular Structure, Sequencing, and Synthesis Facility). Oligonucleotides SEQ ID NO: 3 (encoding the N-terminal sequence TDLNKLV, SEQ ID NO: 25) and SEQ ID NO: 4 (in the center of the pckA gene) (Table 3) were used as primers to amplify the 5'-end of pckA using *A. succinogenes* 130Z chromosomal DNA as the template. The 1.0 kb PCR product was cloned into pCR™II and sequenced. In step (iii), pckA's 3'-end was amplified by an extender PCR approach (Brown, A. J. H., et al., Biotechniques 26:804–806 (1999)) as follows: *A. succinogenes* 130Z chromosomal DNA was digested by EcoRI, EcoRI extremities were annealed to oligonucleotides SEQ ID NO: 5 and SEQ ID NO: 6 (Table 3), 3'-ends were blocked with ddATP, and two successive amplifications were performed, first with primers SEQ ID NO: 7 and SEQ ID NO: 8, then with primers SEQ ID NO: 9 and SEQ ID NO: 10 (Table 3). The final, 2.3-kb PCR product was cloned into pCR™II and sequenced. In step (iv), pckA's promoter region was amplified by extender PCR. The EcoRI-digested, annealed, and blocked *A. succinogenes* 130Z chromosomal DNA from step (iii) was used as the template in two successive amplifications, first with primers SEQ ID NO: 8 and SEQ ID NO: 11, then with primers SEQ ID NO: 10 and SEQ ID NO: 12 (Table 3). The final, 2.0-kb PCR product was cloned into pCR™II and sequenced.

TABLE 3

| SEQ ID NO: | Primer sequence (5' to 3')[a] | Properties |
|---|---|---|
| 1 | GGTAYGGNGGNGARATGAARAARG | pckA non-coding strand, encodes YGGEMKK |
| 2 | CCRTTCCANCCNGTRTT | pckA non-coding strand, encodes NTGWNG |
| 3 | ATGCANGAYYTNAYAARYT | pckA non-coding strand, encodes the N-terminal sequence TDLNKLV |
| 4 | TCCGCGGTTAAGAAAATCACTTT | pckA coding strand, encodes KVIFLT |
| 5 | AATTTGCATGTC | Extender PCR EcoR1 linker |
| 6 | TGCGAGTAAGGATCCTCACGCAAGGA ATTCCGACCAGACATGCA | Extender PCR EcoR1 adaptor |
| 7 | CACATCGACAACATCGTTCGTC | pckA non-coding strand, encodes HIDNIVR |
| 8 | TGCGAGTAAGGATCCTGACGCA | Extender PCR primer P1 |
| 9 | GTATTGCCGCCGGTTTCAAAACTG | pckA non-coding strand, encodes LPPVSKL |
| 10 | CGCAAGGAATTCCGACCAGACA | Extender PCR primer P2 |
| 11 | CGACCGGTAAAAATCCCCGTATCG | pckA coding strand, encodes DTGIFTGR |
| 12 | CCAAACCCGGTTTGGTTTCTTCC | pckA coding strand, encodes LGLTDVKE |
| 13 | CTTTAATCGGAAGCTTTCGATAAATTG AAAATGCAG | Non-coding strand, upstream of pckA, sequence AAGCTT creates a HindIII site |
| 14 | GTCAGTTCTAGATCACCTCATTGATAAT TTAAAATTAAA | Coding strand, upstream of pckA, sequence TCTAGA creates an XbaI site |
| 15 | CAATGAGGTCTAGAATGACTGACTTAAAC AAACTCG | pckA non-coding strand, sequence TCTAGA creates an XbaI site upstream of the ATG start codon |
| 16 | CAAAAGCCCGGGTGGAAATACTCAGCCTT ATTTTTC | Coding strand, downstream of pckA, sequence CCCGGG creates an XmaI site |
| 17 | TTTCTAGAATGCTGGCCGTCGTTTTACAAC GTCGTGACTACTGG | In pUC19, sequence TCTAGA creates an XbaI site upstream of laZα's ATG start codon |
| 18 | CCACATTTACCCGGGACCCAAA AAAGAC TTAC | In pUC19, sequence CCCGGG creates an XmaI site downstream of laZα |
| 19 | AAGCTTTCTGCTAATCCTGTTACCAGTGGG | In pPROEX-1, sequence AAGCTT creates a HindIII site |
| 20 | AAGCTTCCGCATCAGGCGCTCTTCGCGTTC | In pPROEX-1, sequence AAGCTT creates a HindIII site |
| 31 | TCTAGAATGAAATCTAACAATGCGCTC | In pBR325, creates an XbaI site upstream of Tet[R]'s start codon |
| 32 | GAGCTCTCAGGT CGAGGTGGCCCGG | In pBR325, creates a Sac site downstream of Tet[R] |
| 33 | TCTAGAATGGAGAAAAAAATCACTGG | In pBR325, creates an XbaI site upstream of Cm[R]'s start codon |
| 34 | GAGCTCTTACGCCCCGCCCTGCCA C | In pBR325, creates a SacI site downstream of Cm[R] |

[a]Where N is A, C, G, or T; R is A or G; and Y is T or C.

The pckA promoter region was amplified using oligonucleotides SEQ ID NO: 13 and SEQ ID NO: 14 (Table 3) as primers and *A. succinogenes* chromosomal DNA as the template. The 230 bp PCR product was cloned into the HindIII and XbaI sites of pGZRS19 to yield plasmid pLGZ901 (4.8 kb). The pckA gene was amplified using oligonucleotides SEQ ID NO: 15 and SEQ ID NO: 16 (Table 3) as primers and *A. succinogenes* chromosomal DNA as the template. The 1.6 kb PCR product was cloned into the XbaI and XmaI sites of pLGZ901 to yield plasmid pLGZ902 (6.4 kb). The plasmid pLG902 has been deposited under the terms of the Budapest Treaty at the ATCC, Manassas, VA on May 19, 2005 with accession number PTA-6720. The lacZα fragment was amplified using oligonucleotides SEQ ID NO: 17 and SEQ ID NO: 18 (Table 3) as primers and pUC19 as the template. The 0.9 kb PCR product was cloned into the XbaI and XmaI sites of pLGZ901 to yield plasmid pLGZ903 (5.7 kb). The ColE1 origin of replication was amplified using oligonucleotides SEQ ID NO: 19 and SEQ ID NO: 20 (Table 3) as primers and pProEx-1 (Invitrogen, Carlsbad, Calif.) as the template. The PCR product (0.55 kb) was cloned into pCR™II. After sequence verification, the HindIII PCR fragment was subcloned into the HindIII site of pLGZ901, yielding plasmid pLGZ920 (5.4 kb). The Tn10 tetracycline resistance gene (Tet$^R$) was amplified using oligonucleotides SEQ ID NO: 31 and SEQ ID NO: 32 as primers and plasmid pBR325 as the template. The 1.2 kb PCR fragment was cloned into pCR2.1. After sequence verification, the PCR fragment was subcloned between the XbaI and SacI sites of pLZG920, yielding plasmid pLGZ921. The Tn9 chloramphenicol resistance gene (Cm$^R$) was amplified using oligonucleotides SEQ ID NO: 33 and SEQ ID NO: 34 as primers and plasmid pBR325 as the template. The 0.65 kb PCR fragment was cloned into pCR2.1. After sequence verification, the PCR fragment was subcloned between the XbaI and SacI sites of pLZG920, yielding plasmid pLGZ922.

The pckA gene is constitutively expressed at high levels in *A. succinogenes* (van der Werf, M. J., et al., Arch. Microbiol. 167:332–342 (1997)), and PEPCK is a key enzyme in succinate production by *A. succinogenes*. For these reasons, and because we needed a strong *A. succinogenes* promoter that could be used in an expression vector, we decided to clone *A. succinogenes* pckA. The complete sequence of *A. succinogenes* pckA and its promoter region is shown in FIG. 1. The 2 kb DNA fragment contained a single, 1,623 bp open reading frame, encoding a 538-residue protein. In BLAST search, this protein showed 85% and 74% identity (91% and 84% similarity) to the *H. influenzae* and *E. coli* PEPCK sequences, respectively (not shown), confirming that we indeed cloned the *A. succinogenes* pcka gene. As expected, the consensus sequences involved in ATP, $Mg^{2+}$, phosphoenolpyruvate, and oxaloacetate binding that are conserved in all ATP/ADP-dependent PEPCKs (Laivenieks, M., et al., Appl. Environ. Microbiol. 63:2273–2280 (1997)) are present in *A. succinogenes* PEPCK (not shown). A few nucleotides upstream of the ATG start codon is the sequence AGGTG that could act as pckA's ribosome binding site. Two pairs of sequences located 83 nt and 24 nt upstream of pckA's start codon, respectively, match the *A. pleuropneumoniae* consensus promoter (Doree, S. M., et al., J. Bacteriol. 183:1983–1989 (2001)) sequences TTRAA (−35) and TATAAT (−10) (FIG. 1). The distances separating the −35 and −10 sequences in these two potential promoter regions (i.e., 15 and 18 nucleotides) are in agreement with the short spacing identified between the −35 and −10 elements of *A. pleuropneumoniae* promoters (Doree, S. M., et al., J. Bacteriol. 183:1983–1989 (2001)).

EXAMPLE 5

*A. succinogenes* 130Z and *E. coli* DH5α cells harboring pLGZ901 and pLGZ920 were inoculated in TS (*A. succinogenes*) and LB (*E. coli*) media without ampicillin and incubated at 37° C. Culture samples were removed at one-hour intervals for numeration. Total cell number was counted on TS-agar (*A. succinogenes*) and LB-agar (*E. coli*), and plasmid-containing cells were counted on TS-agar-ampicillin (25 µg/ml, *A. succinogenes*) and LB-agar-ampicillin (50 µg/ml, *E. coli*).

Figure 4:
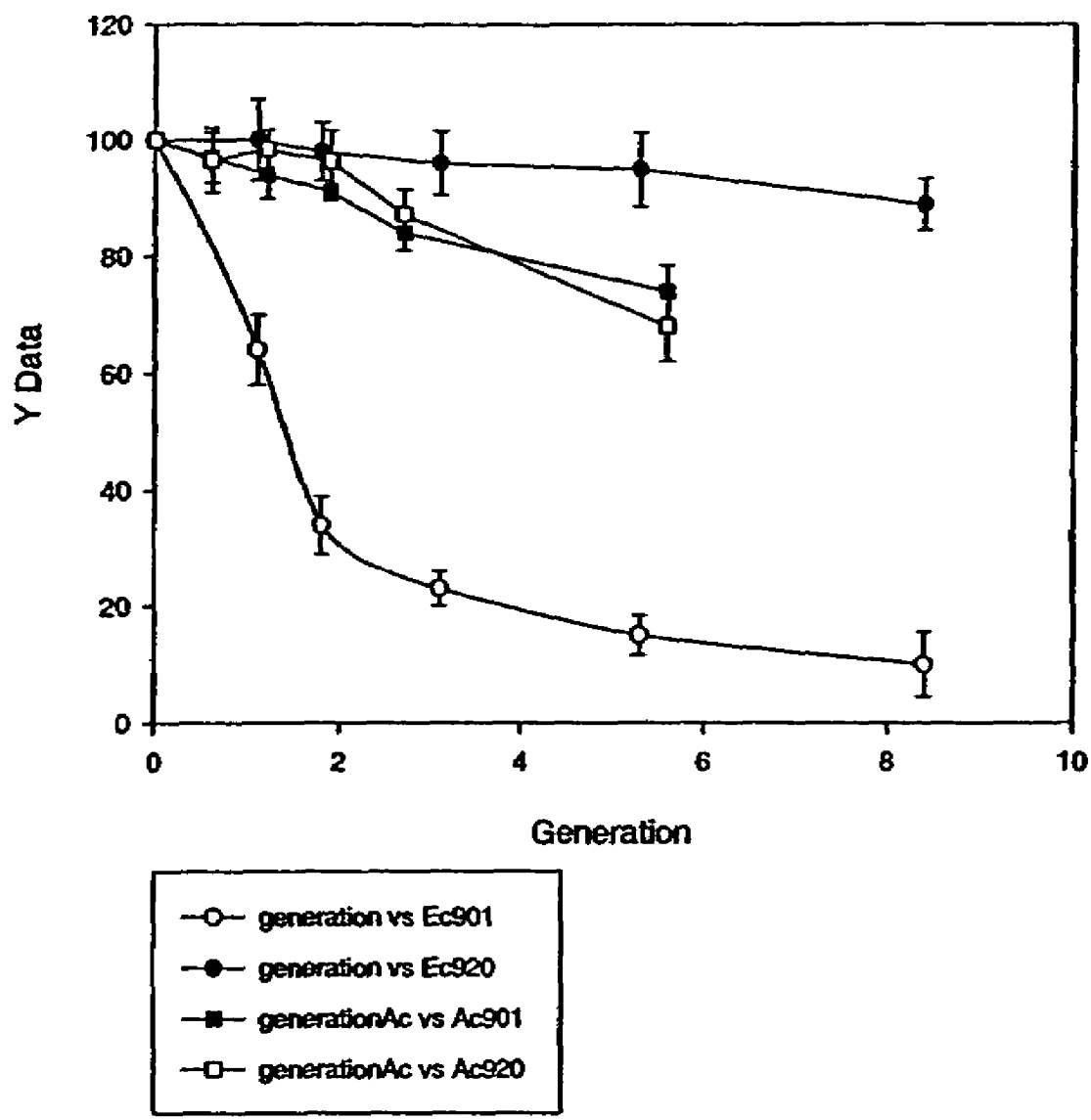
FIG. 4 illustrates the stability of plasmids pLGZ901 and pLGZ920 in *A. succinogenes* and *E. coli*.

The stability of pLGZ901 was tested in *A. succinogenes* 130Z and in *E. coli* DH5α. As shown in FIG. 4, pGLZ901 is much less stable in *E. coli* than in *A. succinogenes*. After five generations of growth in the absence of antibiotic, 70% of the *A. succinogenes* cells still contained the plasmid, whereas fewer than 20% of the *E. coli* cells did. To increase the stability of our vector in *E. coli*, we subcloned the ColE1 origin of replication into pLGZ901's unique HindIII site, yielding plasmid pLGZ920. The stability of pLGZ920 was tested in *A. succinogenes* 130Z and in *E. coli* DH5α (FIG. 4). As expected (ColE1 plasmids are typically not stable in *Actinobacillaceae*), the presence of the ColE1 origin of replication in pLGZ920 did not affect the stability of the plasmid in *A. succinogenes*. In contrast, pLGZ920 was significantly more stable than pLGZ901 in *E. coli*: after 8 generations, while only 10% of *E. coli* cells still contained pLGZ901, 90% still contained pLGZ920.

EXAMPLE 6

β-Galactosidase activity was measured as follows: *A. succinogenes* recombinant strains were grown either in TS broth or in medium A. Thirty microliter aliquots were harvested during the growth time course. The cells were disrupted by vortexing after adding 0.97 ml Z-buffer (60 mM $Na_2HPO_4.7H_2O$, 40 mM $NaH_2PO_4.H_2O$, 10 mM KCl, 1 mM $MgSO_4.7H_2O$, and 50 mM β-mercaptoethanol, pH 7.0), 20 µl chloroform, and 20 µl of 0.1% SDS. The β-galactosidase reaction was initiated by adding 0.2 ml of ONPG solution (4 mg/ml) to the cell lysate. After a thirty minute incubation at 37° C., the reaction was stopped by adding 0.5 ml of 1 M sodium carbonate. The activity was estimated from the absorbance at 420 nm.

To test PEPCK activity, *A. succinogenes* strains were grown in medium A, cells were harvested in the exponential phase, and they were disrupted in a French press as described (van der Werf, M. J., et al., Arch. Microbiol. 167:332–342 (1997)). The PEPCK activity was measured by following the consumption of NADH in a coupled assay at 37° C. The 1 ml reaction mixture consisted of 100 mM Tris (pH 6.6), 35 mM $NaHCO_3$, 16 mM $MgCl_2$, 0.3 mM NADH, 2 U phosphoglycerate phosphokinase/glyceraldehyde phosphate dehydrogenase (Sigma Diagnostics 366-2), 1 mM DTT, 10 mM ADP, 1.8 mM 3-phosphoglycerate (Sigma Diagnostics 366-1), 5 mM PEP, and the cell extract. The extinction coefficient for NADH was 6.22 cm$^{-1}$ mM$^{-1}$ at 340 nm. Protein concentrations were determined using the Bio-Rad Protein Assay kit (Richmond, Calif.) using bovine serum albumin (BSA) as the standard.

Figure 2:
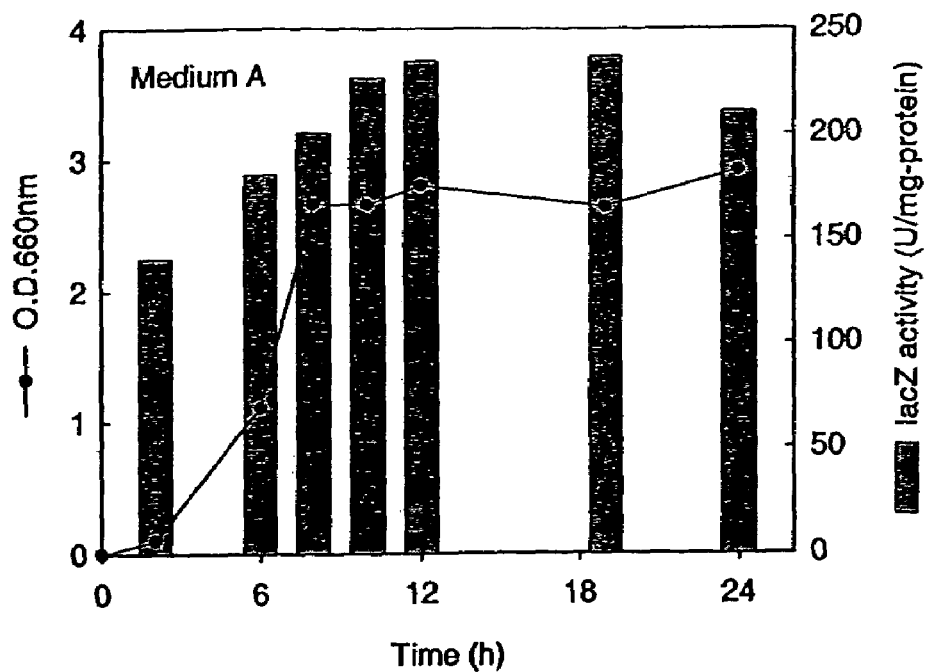
FIG. 2 illustrates β-Galactosidase activity in *A. succinogenes* 130Z grown in medium A.
Figure 3:
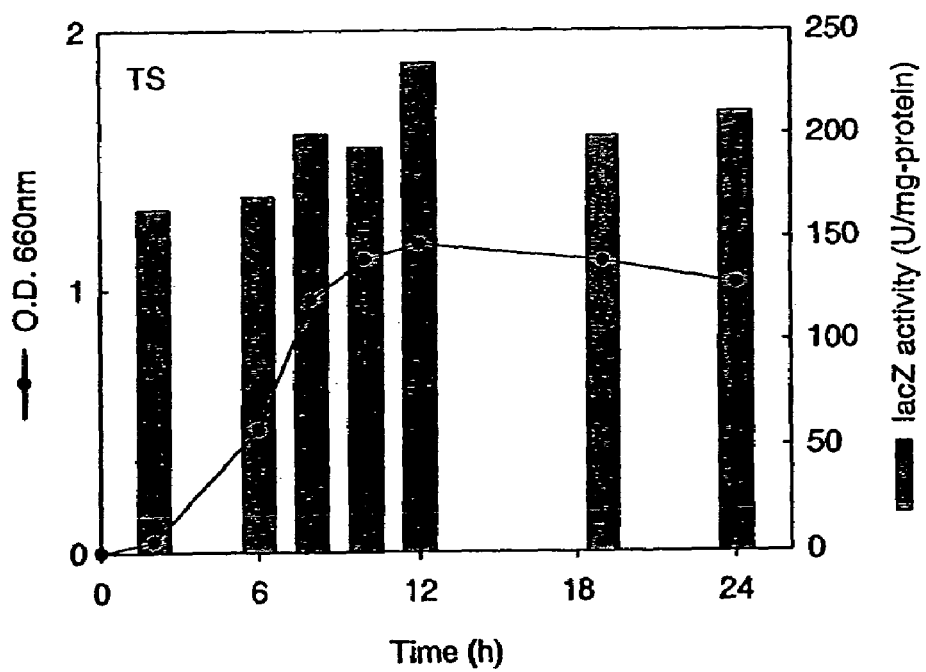
FIG. 3 illustrates β-Galactosidase activity in *A. succinogenes* 130Z grown in TS broth.

Since we could reproducibly introduce plasmid pGZRS-19 into *A. succinogenes* by electroporation, and since pGZRS-19 is stably maintained in *A. succinogenes*, we tested it as an expression vector in *A. succinogenes*. In a first step, we subcloned the pckA promoter region into pGZRS-19, yielding plasmid pLGZ901. Because we did not know which of the two putative promoter regions was the pckA promoter, we subcloned a fragment that encompassed both putative promoters (FIG. 1). This fragment also contained the pckA putative ribosome-binding site. The *A. succinogenes* pckA and *E. coli* lacZα open reading frames were then cloned downstream of the pckA promoter and ribosome binding site in pLGZ901, yielding plasmids pLGZ902 and pLGZ903, respectively. Electroporation of *A. succinogenes* with pLGZ901 and pLGZ903 gave transformation efficiencies similar to those obtained with pGZRS-19 (Table 4).

β-Galatosidase activity was followed in cultures of *A. succinogenes* 130Z comprising pLGZ903, grown in medium A and TS broth (FIG. 2). β-Galactosidase activity was up to 150 units per mg-protein after only 2 hours growth. It then leveled off between 200 and 250 units per mg-protein after 8 hours. No difference in activity was observed between the cultures grown in glucose-based and TS media. Similar β-galactosidase activity levels were observed in *A. succinogenes* FZ6 comprising pLGZ903, grown in the same conditions. These results indicate that the pckA promoter-ribosome binding site cassette allows the expression of a foreign protein at high levels in *A. succinogenes*. These results were verified by testing the activity of PEPCK in *A. succinogenes* strains 130Z and FZ6 comprising plasmid pLZG902. As seen in Table 5, 130Z and FZ6 comprising pLZG902 showed twice as much PEPCK activity as the strains devoid of plasmid.

TABLE 5

PEPCK activity in *A. succinogenes* strains grown in medium A

| Strain | PEPCK activity (nmole/min · mg protein) |
|---|---|
| 130Z | 732 ± 26 |
| 130Z(pLZ902) | 1470 ± 34 |

TABLE 5-continued

PEPCK activity in *A. succinogenes* strains grown in medium A

| Strain | PEPCK activity (nmole/min · mg protein) |
|---|---|
| FZ6 | 851 ± 19 |
| FZ6(pLZ902) | 1591 ± 27 |

EXAMPLE 7

Expression of Tet$^R$ and Cm$^R$ in *A. succinogenes*. We need several markers to conveniently engineer *A. succinogenes*. One can be used to label a gene deletion, while another one can be used to select for the maintenance of a recombinant gene on a plasmid replicon. To determine whether, once expressed, Cm$^R$ and Tet$^R$ could be used as selective markers in *A. succinogenes*, the Tn9 Cm$^R$ and Tn10 Tet$^R$ genes were cloned into pLGZ920 under control of the *A. succinogenes* pckA promoter, yielding plasmids pLGZ921 and pLGZ922, respectively. After electroporation, *A. succinogenes* 130Z cells harboring pLGZ921 and pLGZ922 were spread on TS-agar (30 g/l TS, 10 g/l glucose) plates containing variable amounts of tetracycline and chloramphenicol (FIG. 9). Strains 130Z(pLGZ921) plated on chloramphenicol plates and 130Z(pLGZ922) plated on tetracycline plates were used as the negative controls. As seen in FIG. 9, tetracycline-sensitive 130Z(pLGZ922) strain grew on plates containing up to 1.0 μg/ml tetracycline, but showed no growth after one week on plates containing higher tetracycline concentrations. In contrast, strain 130Z(pLGZ921) grew on plates containing up to 5.0 μg/ml tetracycline. Chloramphenicol-sensitive 130Z(pLGZ921) strain grew on plates containing up to 0.4 μg/ml tetracycline, but not on plates containing higher chloramphenicol concentrations. Strain 130Z (pLGZ922) grew on plates containing up to 5.0 μg/ml chloramphenicol. These results indicate that, once under control of the *A. succinogenes* pckA promoter, the Tn10 Tet$^R$ and Tn9 Cm$^R$ genes are expressed and functional in *A. succinogenes*. These results also suggest that these two genes expressed under control of the pckA promoter can be used as selective markers in media containing the corresponding antibiotic at 1.5 to 4.0 μg/ml.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. An isolated polypeptide which comprises the amino acid sequence set forth in SEQ ID NO: 22.

* * * * *

UNITED STATES PATENT AND TRADEMARK OFFICE
CERTIFICATE OF CORRECTION

| | |
|---|---|
| PATENT NO. | : 7,105,329 B2 |
| APPLICATION NO. | : 11/042925 |
| DATED | : September 12, 2006 |
| INVENTOR(S) | : J. Gregory Zeikus et al. |

It is certified that error appears in the above-identified patent and that said Letters Patent is hereby corrected as shown below:

In the Specification:

At column 1, line 14, please insert:

-- This application is a divisional of copending application(s) application number 10/911,961 filed on 08/05/04. --

-- The nonprovisional application designated above, namely application 10/911,961, filed 08/05/04, claims the benefit of U.S. Provisional Application(s) No(s).: 60/492,804 filed on 08/06/03. --

Signed and Sealed this
Fifteenth Day of March, 2016

Michelle K. Lee
*Director of the United States Patent and Trademark Office*

SEQUENCE LISTING

<160> NUMBER OF SEQ ID NOS: 34

<210> SEQ ID NO 1
<211> LENGTH: 24

```
<212> TYPE: DNA
<213> ORGANISM: Artificial
<220> FEATURE:
<223> OTHER INFORMATION: pckA non-coding strand, encodes YGGEMKK
<220> FEATURE:
<221> NAME/KEY: misc_feature
<222> LOCATION: (5)..(5)
<223> OTHER INFORMATION: any pyrimidine
<220> FEATURE:
<221> NAME/KEY: misc_feature
<222> LOCATION: (8)..(8)
<223> OTHER INFORMATION: any nucleotide
<220> FEATURE:
<221> NAME/KEY: misc_feature
<222> LOCATION: (11)..(11)
<223> OTHER INFORMATION: any nucleotide
<220> FEATURE:
<221> NAME/KEY: misc_feature
<222> LOCATION: (14)..(14)
<223> OTHER INFORMATION: any purine
<220> FEATURE:
<221> NAME/KEY: misc_feature
<222> LOCATION: (20)..(20)
<223> OTHER INFORMATION: any purine
<220> FEATURE:
<221> NAME/KEY: misc_feature
<222> LOCATION: (23)..(23)
<223> OTHER INFORMATION: any purine

<400> SEQUENCE: 1
ggtayggngg ngaratgaar aarg                                            24

<210> SEQ ID NO 2
<211> LENGTH: 17
<212> TYPE: DNA
<213> ORGANISM: Artificial
<220> FEATURE:
<223> OTHER INFORMATION: pckA non-coding strand, encodes NTGWNG
<220> FEATURE:
<221> NAME/KEY: misc_feature
<222> LOCATION: (3)..(3)
<223> OTHER INFORMATION: any purine
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (12)..(12)
<223> OTHER INFORMATION: any nucleotide
<220> FEATURE:
<221> NAME/KEY: misc_feature
<222> LOCATION: (15)..(15)
<223> OTHER INFORMATION: any purine

<400> SEQUENCE: 2
ccrttccanc cngtrtt                                                    17

<210> SEQ ID NO 3
<211> LENGTH: 19
<212> TYPE: DNA
<213> ORGANISM: Artificial
<220> FEATURE:
<223> OTHER INFORMATION: pckA non-coding strand, encodes N-terminal
      sequence TDLNKLV
<220> FEATURE:
<221> NAME/KEY: misc_feature
<222> LOCATION: (6)..(6)
<223> OTHER INFORMATION: any nucleotide
<220> FEATURE:
<221> NAME/KEY: misc_feature
<222> LOCATION: (9)..(9)
<223> OTHER INFORMATION: any pyrimidine
<220> FEATURE:
<221> NAME/KEY: misc_feature
```

```
<222> LOCATION: (10)..(10)
<223> OTHER INFORMATION: any pyrimidine
<220> FEATURE:
<221> NAME/KEY: misc_feature
<222> LOCATION: (12)..(12)
<223> OTHER INFORMATION: any nucleotide
<220> FEATURE:
<221> NAME/KEY: misc_feature
<222> LOCATION: (14)..(14)
<223> OTHER INFORMATION: any pyrimidine
<220> FEATURE:
<221> NAME/KEY: misc_feature
<222> LOCATION: (17)..(17)
<223> OTHER INFORMATION: any purine
<220> FEATURE:
<221> NAME/KEY: misc_feature
<222> LOCATION: (18)..(18)
<223> OTHER INFORMATION: any pyrimidine

<400> SEQUENCE: 3
atgcangayy tnayaaryt                                              19

<210> SEQ ID NO 4
<211> LENGTH: 23
<212> TYPE: DNA
<213> ORGANISM: Artificial
<220> FEATURE:
<223> OTHER INFORMATION: pckA coding strand, encodes KVIFLT

<400> SEQUENCE: 4
tccgcggtta agaaaatcac ttt                                         23

<210> SEQ ID NO 5
<211> LENGTH: 12
<212> TYPE: DNA
<213> ORGANISM: Artificial
<220> FEATURE:
<223> OTHER INFORMATION: extender PCR EcoR1 linker

<400> SEQUENCE: 5
aatttgcatg tc                                                     12

<210> SEQ ID NO 6
<211> LENGTH: 44
<212> TYPE: DNA
<213> ORGANISM: Artificial
<220> FEATURE:
<223> OTHER INFORMATION: extender PCR EcoR1 adaptor

<400> SEQUENCE: 6
tgcgagtaag gatcctcacg caaggaattc cgaccagaca tgca                  44

<210> SEQ ID NO 7
<211> LENGTH: 22
<212> TYPE: DNA
<213> ORGANISM: Artificial
<220> FEATURE:
<223> OTHER INFORMATION: pckA non-coding strand, encodes HIDNIVR

<400> SEQUENCE: 7
cacatcgaca acatcgttcg tc                                          22

<210> SEQ ID NO 8
<211> LENGTH: 22
<212> TYPE: DNA
<213> ORGANISM: Artificial
<220> FEATURE:
<223> OTHER INFORMATION: extender PCR primer P1
```

-continued

```
<210> SEQ ID NO 9
<211> LENGTH: 24
<212> TYPE: DNA
<213> ORGANISM: Artificial
<220> FEATURE:
<223> OTHER INFORMATION: pckA non-coding strand, encodes LPPVSKL

<400> SEQUENCE: 9
gtattgccgc cggtttcaaa actg                                          24

<210> SEQ ID NO 10
<211> LENGTH: 22
<212> TYPE: DNA
<213> ORGANISM: Artificial
<220> FEATURE:
<223> OTHER INFORMATION: extender PCR primer P2

<400> SEQUENCE: 10
cgcaaggaat tccgaccaga ca                                            22

<210> SEQ ID NO 11
<211> LENGTH: 24
<212> TYPE: DNA
<213> ORGANISM: Artificial
<220> FEATURE:
<223> OTHER INFORMATION: pckA coding strand, encodes DTGIFTGR

<400> SEQUENCE: 11
cgaccggtaa aaatccccgt atcg                                          24

<210> SEQ ID NO 12
<211> LENGTH: 23
<212> TYPE: DNA
<213> ORGANISM: Artificial
<220> FEATURE:
<223> OTHER INFORMATION: pckA coding strand, encodes LGLTDVKE

<400> SEQUENCE: 12
ccaaacccgg tttggtttct tcc                                           23

<210> SEQ ID NO 13
<211> LENGTH: 36
<212> TYPE: DNA
<213> ORGANISM: Artificial
<220> FEATURE:
<223> OTHER INFORMATION: Non-coding strand, upstream of pckA, sequence
      AAGCTT creates a HindIII site

<400> SEQUENCE: 13
ctttaatcgg aagctttcga taaattgaaa atgcag                             36

<210> SEQ ID NO 14
<211> LENGTH: 39
<212> TYPE: DNA
<213> ORGANISM: Artificial
<220> FEATURE:
<223> OTHER INFORMATION: coding strand, upstream of pckA, sequence
      TCTAGA creates an Xba I site.

<400> SEQUENCE: 14
gtcagttcta gatcacctca ttgataattt aaaattaaa                          39
```

<400> SEQUENCE: 8
tgcgagtaag gatcctgacg ca                                            22

```
<210> SEQ ID NO 15
<211> LENGTH: 36
<212> TYPE: DNA
<213> ORGANISM: Artificial
<220> FEATURE:
<223> OTHER INFORMATION: pckA non-coding strand, sequence TCTAGA creates
      an XbaI site upstream of the ATG start codon.

<400> SEQUENCE: 15
caatgaggtc tagaatgact gacttaaaca aactcg                                    36

<210> SEQ ID NO 16
<211> LENGTH: 36
<212> TYPE: DNA
<213> ORGANISM: Artificial
<220> FEATURE:
<223> OTHER INFORMATION: Coding strand, downstream of pckA, sequence
      CCCGGG creates an XmaI site.

<400> SEQUENCE: 16
caaaagcccg ggtggaaata ctcagcctta tttttc                                    36

<210> SEQ ID NO 17
<211> LENGTH: 44
<212> TYPE: DNA
<213> ORGANISM: Artificial
<220> FEATURE:
<223> OTHER INFORMATION: In pUC19, sequence TCTAGA creates an XbaI site
      upstream of LacZ (alpha) ATG start codon.

<400> SEQUENCE: 17
tttctagaat gctggccgtc gttttacaac gtcgtgacta ctgg                           44

<210> SEQ ID NO 18
<211> LENGTH: 32
<212> TYPE: DNA
<213> ORGANISM: Artificial
<220> FEATURE:
<223> OTHER INFORMATION: In pUC19, sequence CCCGGG creates an XmaI site
      downstream of LacZ (alpha).

<400> SEQUENCE: 18
ccacatttac ccgggaccca aaaaagactt ac                                       32

<210> SEQ ID NO 19
<211> LENGTH: 30
<212> TYPE: DNA
<213> ORGANISM: Artificial
<220> FEATURE:
<223> OTHER INFORMATION: In pPROEX-1, sequence AAGCTT creates a HindIII
      site.

<400> SEQUENCE: 19
aagctttctg ctaatcctgt taccagtggg                                          30

<210> SEQ ID NO 20
<211> LENGTH: 30
<212> TYPE: DNA
<213> ORGANISM: Artificial
<220> FEATURE:
<223> OTHER INFORMATION: In pPROEX-1, sequence AAGCTT creates a HindIII
      site.

<400> SEQUENCE: 20
aagcttccgc atcaggcgct cttcgcgttc                                          30

<210> SEQ ID NO 21
```

-continued

```
<211> LENGTH: 2048
<212> TYPE: DNA
<213> ORGANISM: Actinobacillus succinogenes
<220> FEATURE:
<221> NAME/KEY: promoter
<222> LOCATION: (150)..(154)
<223> OTHER INFORMATION: putative promoter -35
<220> FEATURE:
<221> NAME/KEY: promoter
<222> LOCATION: (170)..(175)
<223> OTHER INFORMATION: putative promoter -10
<220> FEATURE:
<221> NAME/KEY: promoter
<222> LOCATION: (206)..(210)
<223> OTHER INFORMATION: putative promoter -35
<220> FEATURE:
<221> NAME/KEY: promoter
<222> LOCATION: (229)..(234)
<223> OTHER INFORMATION: putative promoter -10
<220> FEATURE:
<221> NAME/KEY: RBS
<222> LOCATION: (250)..(254)
<223> OTHER INFORMATION: putative ribosome binding site
<220> FEATURE:
<221> NAME/KEY: terminator
<222> LOCATION: (1873)..(1875)
<223> OTHER INFORMATION: stop codon

<400> SEQUENCE: 21
ttaatttctt taatcgggac gctatcgata aattgaaaat gcagcaatag aggaaacacg      60
gtttgtttga gtgaaaacag ccgtgttttt tcatttaccg ccataaaaat ttgaaacgga     120
tcacaaatca tgaaaaaaat acgttcaaat tagaactaat tatcgaaaat ttgatctagt     180
taacattttt taggtataaa tagttttaaa atagatctag tttggatttt taattttaaa    240
ttatcaatga ggtgaagtat gactgactta acaaactcg ttaaagaact taatgactta     300
gggcttaccg atgttaagga aattgtgtat aacccgagtt atgaacaact tttcgaggaa    360
gaaaccaaac cgggtttgga gggtttcgat aaagggacgt taaccacgct tggcgcggtt    420
gccgtcgata cggggatttt taccggtcgt tcaccgaaag ataaatatat cgtttgcgat    480
gaaactacga agacaccgt ttggtggaac agcgaagcgg cgaaaaacga taacaaaccg     540
atgacgcaag aaacttggaa aagtttgaga gaattagtgg cgaaacaact ttccggtaaa    600
cgtttattcg tggtagaagg ttactgcggc gccagtgaaa acaccgtat cggtgtgcgt      660 atggttactg aagtggcatg gcaggcgcat tttgtgaaaa acatgtttat ccgaccgacc    720
gatgaagagt tgaaaaattt caaagcggat tttaccgtgt taaacggtgc taaatgtact    780
aatccgaact ggaaagaaca aggtttgaac agtgaaaact ttgtcgcttt caatattacc    840
gaaggtattc agcttatcgg cggtacttgg tacggcggtg aaatgaaaaa aggtatgttc    900
tcaatgatga actacttcct gccgttaaaa ggtgtggctt ccatgcactg ttccgccaac    960
gtaggtaaag acggtgacgt ggctattttc ttcggtttat ccggtacggg taaaacaacg   1020
ctttcgaccg atcctaaacg ccaattaatc ggtgatgacg aacacggttg ggatgaatcc    1080
ggcgtattta actttgaagg cggttgttac gcgaaaacca ttaacttatc tcaagaaaac    1140
gaaccggata tttacggcgc aatccgtcgt gacgcattat tagaaaacgt cgtggttcgt    1200
gcagacggtt ccgttgactt tgacgacggt tcaaaaacag aaaatacccg tgtttcatat    1260
ccgatttacc acatcgacaa catcgttcgt ccggtatcga aagccggtca tgcaaccaaa    1320
gtgattttct taccgcgga cgcattcggc gtattgccgc cggtttcaaa actgactccg     1380
gaacaaaccg aatactactt cttatccggc tttactgcaa aattagcggg tacgaacgc     1440 ggcgtaaccg aaccgactcc gacattctcg gcctgtttcg gtgcggcatt cttaagcctg   1500
```

-continued

```
catccgattc aatatgcgga cgtgttggtc gaacgcatga aagcctccgg tgcggaagct    1560
tatttggtga acaccggttg aacggcacg ggtaaacgta tttcaatcaa agatacccgc    1620
ggtattatcg atgcgatttt ggacggttca atcgaaaaag cggaaatggg cgaattgcca    1680
atctttaatt tagcgattcc taaagcatta ccgggtgttg atcctgctat tttggatccg    1740
cgcgatactt acgcagacaa agcgcaatgg caagttaaag cggaagattt ggcaaaccgt    1800
ttcgtgaaaa actttgtgaa atatacggcg aatccggaag cggctaaatt agttggcgcc    1860
ggtccaaaag cataaaactg taaaagcata gtatgtgcat gattcggtaa actaccgaat    1920
aaaatctgaa aaataaggct gagtatttcc actcagcctt ttgttttgga aattagaagt    1980
tgtttagaaa gataaacggc gcggcttatt cgtcgtatta tttgggacat aaaaaacccg    2040
ttgataaa                                                              2048
```

<210> SEQ ID NO 22
<211> LENGTH: 538
<212> TYPE: PRT
<213> ORGANISM: Actinobacillus succinogenes

<400> SEQUENCE: 22

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Glu Gly Tyr Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270
```

-continued

```
Glu Ser Gly Val Phe Asn Phe Glu Gly Gly Cys Tyr Ala Lys Thr Ile
            275                 280                 285

Asn Leu Ser Gln Glu Asn Glu Pro Asp Ile Tyr Gly Ala Ile Arg Arg
        290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
        515                 520                 525

Ala Lys Leu Val Gly Ala Gly Pro Lys Ala
    530                 535
```

<210> SEQ ID NO 23
<211> LENGTH: 7
<212> TYPE: PRT
<213> ORGANISM: Artificial
<220> FEATURE:
<223> OTHER INFORMATION: encoded on primer 1

<400> SEQUENCE: 23

```
Tyr Gly Gly Glu Met Lys Lys
1               5
```

<210> SEQ ID NO 24
<211> LENGTH: 6
<212> TYPE: PRT
<213> ORGANISM: Artificial
<220> FEATURE:
<223> OTHER INFORMATION: encoded on primer 2

<400> SEQUENCE: 24

```
Asn Thr Gly Trp Asn Gly
1               5
```

```
<210> SEQ ID NO 25
<211> LENGTH: 7
<212> TYPE: PRT
<213> ORGANISM: Artificial
<220> FEATURE:
<223> OTHER INFORMATION: encoded on primer 3

<400> SEQUENCE: 25

Thr Asp Leu Asn Lys Leu Val
1               5

<210> SEQ ID NO 26
<211> LENGTH: 6
<212> TYPE: PRT
<213> ORGANISM: Artificial
<220> FEATURE:
<223> OTHER INFORMATION: encoded by primer 4

<400> SEQUENCE: 26

Lys Val Ile Phe Leu Thr
1               5

<210> SEQ ID NO 27
<211> LENGTH: 7
<212> TYPE: PRT
<213> ORGANISM: Artificial
<220> FEATURE:
<223> OTHER INFORMATION: encoded by primer 8

<400> SEQUENCE: 27

His Ile Asp Asn Ile Val Arg
1               5

<210> SEQ ID NO 28
<211> LENGTH: 7
<212> TYPE: PRT
<213> ORGANISM: Artificial
<220> FEATURE:
<223> OTHER INFORMATION: encoded by primer 9

<400> SEQUENCE: 28

Leu Pro Pro Val Ser Lys Leu
1               5

<210> SEQ ID NO 29
<211> LENGTH: 8
<212> TYPE: PRT
<213> ORGANISM: Artificial
<220> FEATURE:
<223> OTHER INFORMATION: encoded by primer 11

<400> SEQUENCE: 29

Asp Thr Gly Ile Phe Thr Gly Arg
1               5

<210> SEQ ID NO 30
<211> LENGTH: 8
<212> TYPE: PRT
<213> ORGANISM: Artificial
<220> FEATURE:
<223> OTHER INFORMATION: encoded by primer 12

<400> SEQUENCE: 30

Leu Gly Leu Thr Asp Val Lys Glu
1               5

<210> SEQ ID NO 31
```

-continued

```
<211> LENGTH: 27
<212> TYPE: DNA
<213> ORGANISM: Artificial
<220> FEATURE:
<223> OTHER INFORMATION: Tetracyclin PCR primer 1

<400> SEQUENCE: 31
tctagaatga aatctaacaa tgcgctc                                27

<210> SEQ ID NO 32
<211> LENGTH: 25
<212> TYPE: DNA
<213> ORGANISM: Artificial
<220> FEATURE:
<223> OTHER INFORMATION: Tetracyclin PCR primer 2

<400> SEQUENCE: 32
gagctctcag gtcgaggtgg cccgg                                  25

<210> SEQ ID NO 33
<211> LENGTH: 26
<212> TYPE: DNA
<213> ORGANISM: Artificial
<220> FEATURE:
<223> OTHER INFORMATION: Chloramphenicol PCR primer 1

<400> SEQUENCE: 33
tctagaatgg agaaaaaaat cactgg                                 26

<210> SEQ ID NO 34
<211> LENGTH: 25
<212> TYPE: DNA
<213> ORGANISM: Artificial
<220> FEATURE:
<223> OTHER INFORMATION: Chloramphenicol PCR primer 2

<400> SEQUENCE: 34
gagctcttac gccccgccct gccac                                  25
```